(12) United States Patent
Condurso et al.

(10) Patent No.: US 9,307,907 B2
(45) Date of Patent: Apr. 12, 2016

(54) SYSTEM AND METHOD FOR DYNAMICALLY ADJUSTING PATIENT THERAPY

(71) Applicant: CareFusion 303, Inc., San Diego, CA (US)

(72) Inventors: Joseph Condurso, Olivenhain, CA (US); Cynthia Yamaga, Oceanside, CA (US); Robert Butterfield, Poway, CA (US); Simon Morling, Bradford on Avon (GB); Clifton Pait, San Diego, CA (US); Patricia West, Santee, CA (US); Timothy W. Vanderveen, Poway, CA (US); Richard Crass, San Diego, CA (US)

(73) Assignee: CareFusion 303,Inc., San Diego, CA (US)

( * ) Notice: Subject to any disclaimer, the term of this patent is extended or adjusted under 35 U.S.C. 154(b) by 0 days.

(21) Appl. No.: 14/306,125

(22) Filed: Jun. 16, 2014

(65) Prior Publication Data

US 2014/0297313 A1    Oct. 2, 2014

Related U.S. Application Data

(63) Continuation of application No. 14/103,816, filed on Dec. 11, 2013, now Pat. No. 8,761,906, which is a continuation of application No. 13/705,032, filed on Dec. 4, 2012, now Pat. No. 8,630,722, which is a

(51) Int. Cl.
*G05B 13/02* (2006.01)
*A61M 31/00* (2006.01)
(Continued)

(52) U.S. Cl.
CPC .............. *A61B 5/0002* (2013.01); *A61B 5/002* (2013.01); *A61B 5/021* (2013.01); *A61B 5/4848* (2013.01);
(Continued)

(58) Field of Classification Search
CPC . G06F 19/3468; G06F 19/324; A61B 5/4848; A61B 5/0002; A61B 5/746; A61M 5/14
USPC .................................. 700/28; 604/66; 600/26
See application file for complete search history.

(56) References Cited

U.S. PATENT DOCUMENTS

2,141,006 A   12/1938  Marinsky
3,724,455 A    4/1973  Unger
(Continued)

FOREIGN PATENT DOCUMENTS

CA    2472098 A1    7/2003
CA    2554903 A1    4/2005
(Continued)

OTHER PUBLICATIONS

International Search Report and Written Opinion of the International Searching Authority dated Sep. 5, 2014 for PCT application PCT/US2014/037577.

(Continued)

*Primary Examiner* — Ronald Hartman, Jr.
(74) *Attorney, Agent, or Firm* — McDermott Will & Emery LLP

(57) ABSTRACT

A system and method of managing therapy provided to patients in an institution. The system monitors all aspects of the medication delivery to a patient, as well as other information related to the patient, such as values of vital signs, laboratory results and patient factors such as history, diagnosis, allergies and the like. The system includes one or more databases of information, including institutionally developed rules, guidelines and protocol representing the best medical practices of the institution. The system provides alerts and/or recommendations based on the application of the rules to the information being monitored, and alerts care givers accordingly, providing for dynamic adjustment of the patient's therapy. The system also monitors the status of the alerts, and if no action is taken in a selected period of time, may escalate the priority of the alert and/or halt the delivery of medication to the patient until the alert is resolved.

21 Claims, 11 Drawing Sheets

Related U.S. Application Data continuation of application No. 12/947,773, filed on Nov. 16, 2010, now Pat. No. 8,340,792, which is a continuation of application No. 10/925,511, filed on Aug. 25, 2004, now Pat. No. 7,860,583.

(51) Int. Cl.

| | | |
|---|---|---|
| *A61M 21/00* | (2006.01) | |
| *A61B 5/00* | (2006.01) | |
| *G06F 19/00* | (2011.01) | |
| *G06Q 50/22* | (2012.01) | |
| *G06Q 50/24* | (2012.01) | |
| *A61B 5/021* | (2006.01) | |
| *A61M 5/172* | (2006.01) | |

(52) U.S. Cl.
CPC ............... *A61B 5/746* (2013.01); *A61M 5/172* (2013.01); *G06F 19/326* (2013.01); *G06F 19/3418* (2013.01); *G06F 19/3456* (2013.01); *G06F 19/3468* (2013.01); *G06F 19/3481* (2013.01); *G06Q 50/22* (2013.01); *G06Q 50/24* (2013.01); *A61M 2205/18* (2013.01); *A61M 2205/3576* (2013.01); *A61M 2205/50* (2013.01); *G06F 19/324* (2013.01); *G06F 19/345* (2013.01); *G06F 19/3406* (2013.01); *G06F 19/3437* (2013.01)

(56) References Cited

U.S. PATENT DOCUMENTS

| | | | |
|---|---|---|---|
| 3,831,006 A | 8/1974 | Chaffin, III et al. | |
| 3,848,112 A | 11/1974 | Weichselbaum et al. | |
| 3,872,448 A | 3/1975 | Mitchell, Jr. | |
| 3,898,984 A | 8/1975 | Mandel et al. | |
| 3,910,260 A | 10/1975 | Sarnoff et al. | |
| 3,921,196 A | 11/1975 | Patterson | |
| 3,970,996 A | 7/1976 | Yasaka et al. | |
| 4,051,522 A | 9/1977 | Healy et al. | |
| 4,135,241 A | 1/1979 | Stanis et al. | |
| 4,164,320 A | 8/1979 | Irazoqui et al. | |
| 4,216,462 A | 8/1980 | McGrath et al. | |
| 4,237,344 A | 12/1980 | Moore | |
| 4,315,309 A | 2/1982 | Coli | |
| 4,321,461 A | 3/1982 | Walter, Jr. et al. | |
| 4,360,125 A | 11/1982 | Martindale et al. | |
| 4,373,527 A | 2/1983 | Fischell | |
| 4,476,381 A | 10/1984 | Rubin | |
| 4,604,847 A | 8/1986 | Moulding, Jr. et al. | |
| 4,636,950 A | 1/1987 | Caswell et al. | |
| 4,674,652 A | 6/1987 | Aten et al. | |
| 4,676,776 A | 6/1987 | Howson | |
| 4,688,026 A | 8/1987 | Scribner et al. | |
| 4,695,954 A | 9/1987 | Rose et al. | |
| 4,696,671 A | 9/1987 | Epstein et al. | |
| 4,731,726 A | 3/1988 | Allen, III | |
| 4,733,364 A | 3/1988 | Yamagata | |
| 4,756,706 A | 7/1988 | Kerns et al. | |
| 4,785,969 A | 11/1988 | McLaughlin | |
| 4,788,449 A | 11/1988 | Katz | |
| 4,803,625 A | 2/1989 | Fu et al. | |
| 4,810,243 A | 3/1989 | Howson | |
| 4,828,545 A | 5/1989 | Epstein et al. | |
| 4,831,562 A | 5/1989 | McIntosh et al. | |
| 4,835,372 A | 5/1989 | Gombrich et al. | |
| 4,839,806 A | 6/1989 | Goldfischer et al. | |
| 4,847,764 A | 7/1989 | Halvorson | |
| 4,850,009 A | 7/1989 | Zook et al. | |
| 4,853,521 A | 8/1989 | Claeys et al. | |
| 4,855,909 A | 8/1989 | Vincent et al. | |
| 4,857,713 A | 8/1989 | Brown | |
| 4,857,716 A | 8/1989 | Gombrich et al. | |
| 4,865,584 A | 9/1989 | Epstein et al. | |
| 4,882,575 A | 11/1989 | Kawahara | |
| 4,899,839 A | 2/1990 | Dessertine et al. | |
| 4,916,441 A | 4/1990 | Gombrich | |
| 4,918,604 A | 4/1990 | Baum | |
| 4,925,444 A | 5/1990 | Orkin et al. | |
| 4,942,544 A | 7/1990 | McIntosh et al. | |
| 4,950,246 A | 8/1990 | Muller | |
| 4,967,928 A | 11/1990 | Carter | |
| 4,970,669 A | 11/1990 | McIntosh et al. | |
| 4,978,335 A | 12/1990 | Arthur, III | |
| 5,001,630 A | 3/1991 | Wiltfong | |
| 5,006,699 A | 4/1991 | Felkner et al. | |
| 5,036,462 A | 7/1991 | Kaufman et al. | |
| 5,036,852 A | 8/1991 | Leishman | |
| 5,072,383 A | 12/1991 | Brimm et al. | |
| 5,077,666 A | 12/1991 | Brimm et al. | |
| 5,078,683 A | 1/1992 | Sancoff et al. | |
| 5,088,056 A | 2/1992 | McIntosh et al. | |
| 5,088,981 A | 2/1992 | Howson et al. | |
| 5,100,380 A | 3/1992 | Epstein et al. | |
| 5,126,957 A | 6/1992 | Kaufman et al. | |
| 5,142,484 A | 8/1992 | Kaufman et al. | |
| 5,153,416 A | 10/1992 | Neeley | |
| 5,153,827 A | 10/1992 | Coutre et al. | |
| 5,164,575 A | 11/1992 | Neeley et al. | |
| 5,166,498 A | 11/1992 | Neeley | |
| 5,171,977 A | 12/1992 | Morrison | |
| 5,181,910 A | 1/1993 | Scanlon | |
| 5,207,642 A | 5/1993 | Orkin et al. | |
| 5,235,507 A | 8/1993 | Sackler et al. | |
| 5,256,157 A | 10/1993 | Samiotes et al. | |
| 5,258,906 A | 11/1993 | Kroll et al. | |
| 5,265,010 A | 11/1993 | Evans-Paganelli et al. | |
| 5,267,174 A | 11/1993 | Kaufman et al. | |
| 5,291,399 A | 3/1994 | Chaco | |
| 5,292,029 A | 3/1994 | Pearson | |
| 5,307,263 A | 4/1994 | Brown | |
| 5,312,334 A | 5/1994 | Hara et al. | |
| 5,314,243 A | 5/1994 | McDonald et al. | |
| 5,315,505 A | 5/1994 | Pratt et al. | |
| 5,317,506 A | 5/1994 | Coutre et al. | |
| H1324 H | 6/1994 | Dalke et al. | |
| 5,331,547 A | 7/1994 | Laszlo | |
| 5,356,378 A | 10/1994 | Doan | |
| 5,367,555 A | 11/1994 | Isoyama | |
| 5,368,554 A | 11/1994 | Nazarian et al. | |
| 5,371,692 A | 12/1994 | Draeger et al. | |
| 5,374,813 A | 12/1994 | Shipp | |
| 5,376,070 A | 12/1994 | Purvis et al. | |
| 5,378,231 A | 1/1995 | Johnson et al. | |
| 5,382,232 A | 1/1995 | Hague et al. | |
| 5,390,238 A | 2/1995 | Kirk et al. | |
| 5,401,059 A | 3/1995 | Ferrario | |
| 5,404,384 A | 4/1995 | Colburn et al. | |
| 5,408,443 A | 4/1995 | Weinberger | |
| 5,412,372 A | 5/1995 | Parkhurst et al. | |
| 5,412,564 A | 5/1995 | Ecer | |
| 5,416,695 A | 5/1995 | Stutman et al. | |
| 5,456,691 A | 10/1995 | Snell | |
| 5,460,605 A | 10/1995 | Tuttle et al. | |
| 5,465,082 A | 11/1995 | Chaco | |
| 5,472,614 A | 12/1995 | Rossi | |
| 5,502,944 A | 4/1996 | Kraft et al. | |
| 5,515,426 A | 5/1996 | Yacenda et al. | |
| 5,522,798 A | 6/1996 | Johnson et al. | |
| 5,533,079 A | 7/1996 | Colburn et al. | |
| 5,536,084 A | 7/1996 | Curtis et al. | |
| 5,538,006 A | 7/1996 | Heim et al. | |
| 5,542,420 A | 8/1996 | Goldman et al. | |
| 5,544,649 A | 8/1996 | David et al. | |
| 5,544,661 A | 8/1996 | Davis et al. | |
| 5,547,470 A * | 8/1996 | Johnson et al. | 604/67 |
| 5,561,412 A | 10/1996 | Novak et al. | |
| 5,562,232 A | 10/1996 | Pearson | |
| 5,564,803 A | 10/1996 | McDonald et al. | |
| 5,573,506 A | 11/1996 | Vasko | |
| 5,582,593 A | 12/1996 | Hultman | |
| 5,583,758 A | 12/1996 | McIlroy et al. | |
| 5,592,374 A | 1/1997 | Fellegara et al. | |
| 5,594,786 A | 1/1997 | Chaco et al. | |

(56) References Cited

U.S. PATENT DOCUMENTS

| | | | |
|---|---|---|---|
| 5,597,995 A | 1/1997 | Williams et al. | |
| 5,601,445 A | 2/1997 | Schipper et al. | |
| 5,622,429 A | 4/1997 | Heinze | |
| 5,628,309 A | 5/1997 | Brown | |
| 5,630,710 A | 5/1997 | Tune et al. | |
| 5,633,910 A | 5/1997 | Cohen | |
| 5,643,212 A | 7/1997 | Coutre et al. | |
| 5,644,778 A | 7/1997 | Burks et al. | |
| 5,645,531 A * | 7/1997 | Thompson | A61M 1/3621 128/DIG. 3 |
| 5,651,775 A | 7/1997 | Walker et al. | |
| 5,655,118 A | 8/1997 | Heindel et al. | |
| 5,657,236 A | 8/1997 | Conkright | |
| 5,658,250 A | 8/1997 | Blomquist et al. | |
| 5,672,154 A | 9/1997 | Sillen et al. | |
| 5,681,285 A | 10/1997 | Ford et al. | |
| 5,683,367 A | 11/1997 | Jordan et al. | |
| 5,685,844 A | 11/1997 | Marttila | |
| 5,689,229 A | 11/1997 | Chaco et al. | |
| 5,692,640 A | 12/1997 | Caulfield et al. | |
| 5,699,038 A | 12/1997 | Ulrich et al. | |
| 5,700,998 A | 12/1997 | Palti | |
| 5,703,786 A | 12/1997 | Conkright | |
| 5,704,352 A | 1/1998 | Tremblay et al. | |
| 5,710,551 A | 1/1998 | Ridgeway | |
| 5,712,913 A | 1/1998 | Chaum | |
| 5,713,856 A | 2/1998 | Eggers et al. | |
| 5,721,913 A | 2/1998 | Ackroff et al. | |
| 5,733,259 A | 3/1998 | Valcke et al. | |
| 5,737,539 A | 4/1998 | Edelson et al. | |
| 5,738,102 A | 4/1998 | Lemelson | |
| 5,752,235 A | 5/1998 | Kehr et al. | |
| 5,758,095 A | 5/1998 | Albaum et al. | |
| 5,758,096 A | 5/1998 | Barsky et al. | |
| 5,760,704 A | 6/1998 | Barton et al. | |
| 5,764,034 A | 6/1998 | Bowman et al. | |
| 5,772,585 A | 6/1998 | Lavin et al. | |
| 5,774,865 A | 6/1998 | Glynn | |
| 5,781,442 A | 7/1998 | Engleson et al. | |
| 5,790,409 A | 8/1998 | Fedor et al. | |
| 5,795,327 A | 8/1998 | Wilson et al. | |
| 5,803,906 A | 9/1998 | Pratt et al. | |
| 5,807,321 A | 9/1998 | Stoker et al. | |
| 5,807,336 A | 9/1998 | Russo et al. | |
| 5,819,229 A | 10/1998 | Boppe | |
| 5,822,418 A | 10/1998 | Yacenda et al. | |
| 5,822,544 A | 10/1998 | Chaco et al. | |
| 5,832,488 A | 11/1998 | Eberhardt | |
| 5,833,599 A | 11/1998 | Schrier et al. | |
| 5,842,173 A | 11/1998 | Strum et al. | |
| 5,842,976 A | 12/1998 | Williamson | |
| 5,845,253 A | 12/1998 | Rensimer et al. | |
| 5,845,254 A | 12/1998 | Lockwood et al. | |
| 5,845,255 A | 12/1998 | Mayaud | |
| 5,845,264 A | 12/1998 | Nellhaus | |
| 5,848,593 A | 12/1998 | McGrady et al. | |
| 5,850,344 A | 12/1998 | Conkright | |
| 5,852,408 A | 12/1998 | Christiansen et al. | |
| 5,855,550 A | 1/1999 | Lai et al. | |
| 5,867,821 A | 2/1999 | Ballantyne et al. | |
| 5,871,465 A | 2/1999 | Vasko | |
| 5,883,806 A | 3/1999 | Meador et al. | |
| 5,885,245 A | 3/1999 | Lynch et al. | |
| 5,894,273 A | 4/1999 | Meador et al. | |
| 5,895,371 A | 4/1999 | Levitas et al. | |
| 5,899,998 A | 5/1999 | McGauley et al. | |
| 5,903,211 A | 5/1999 | Flego et al. | |
| 5,905,653 A | 5/1999 | Higham et al. | |
| 5,907,490 A | 5/1999 | Oliver | |
| 5,911,132 A | 6/1999 | Sloane | |
| 5,911,687 A | 6/1999 | Sato et al. | |
| 5,912,818 A | 6/1999 | McGrady et al. | |
| 5,920,054 A | 7/1999 | Uber, III | |
| 5,920,263 A | 7/1999 | Huttenhoff et al. | |
| 5,928,329 A | 7/1999 | Clark et al. | |
| 5,930,145 A | 7/1999 | Yuyama et al. | |
| 5,935,099 A | 8/1999 | Peterson et al. | |
| 5,941,710 A | 8/1999 | Lampotang et al. | |
| 5,942,986 A | 8/1999 | Shabot et al. | |
| 5,950,630 A | 9/1999 | Portwood et al. | |
| 5,950,632 A | 9/1999 | Reber et al. | |
| 5,953,099 A | 9/1999 | Walach | |
| 5,954,641 A | 9/1999 | Kehr et al. | |
| 5,957,885 A | 9/1999 | Bollish et al. | |
| 5,961,036 A | 10/1999 | Michael et al. | |
| 5,961,446 A | 10/1999 | Beller et al. | |
| 5,971,593 A | 10/1999 | McGrady | |
| 5,985,371 A | 11/1999 | Fujioka et al. | |
| 5,995,077 A | 11/1999 | Wilcox et al. | |
| 6,000,828 A | 12/1999 | Leet | |
| 6,003,006 A | 12/1999 | Colella et al. | |
| 6,009,333 A | 12/1999 | Chaco | |
| 6,021,392 A | 2/2000 | Lester et al. | |
| 6,024,699 A | 2/2000 | Surwit et al. | |
| 6,032,155 A | 2/2000 | de la Huerga | |
| 6,039,251 A | 3/2000 | Holowko et al. | |
| 6,047,203 A | 4/2000 | Sackner et al. | |
| 6,048,087 A | 4/2000 | Laurent et al. | |
| 6,053,887 A | 4/2000 | Levitas et al. | |
| 6,063,026 A | 5/2000 | Schauss et al. | |
| 6,082,776 A | 7/2000 | Feinberg | |
| 6,112,182 A | 8/2000 | Akers et al. | |
| RE36,871 E | 9/2000 | Epstein et al. | |
| 6,134,582 A | 10/2000 | Kennedy | |
| 6,135,949 A | 10/2000 | Russo et al. | |
| 6,202,923 B1 | 3/2001 | Boyer et al. | |
| 6,228,057 B1 | 5/2001 | Vasko | |
| 6,241,704 B1 | 6/2001 | Peterson et al. | |
| 6,269,340 B1 | 7/2001 | Ford et al. | |
| 6,282,441 B1 | 8/2001 | Raymond et al. | |
| 6,290,681 B1 | 9/2001 | Brown | |
| 6,292,698 B1 | 9/2001 | Duffin et al. | |
| 6,302,844 B1 | 10/2001 | Walker et al. | |
| 6,312,378 B1 | 11/2001 | Bardy | |
| 6,314,556 B1 | 11/2001 | DeBusk et al. | |
| 6,319,200 B1 | 11/2001 | Lai et al. | |
| 6,322,502 B1 | 11/2001 | Schoenberg et al. | |
| 6,338,007 B1 | 1/2002 | Broadfield et al. | |
| 6,339,732 B1 | 1/2002 | Phoon et al. | |
| 6,406,426 B1 | 6/2002 | Reuss et al. | |
| 6,421,650 B1 | 7/2002 | Goetz et al. | |
| 6,519,569 B1 | 2/2003 | White et al. | |
| 6,529,892 B1 | 3/2003 | Lambert | |
| 6,540,672 B1 | 4/2003 | Simonsen et al. | |
| 6,558,352 B1 | 5/2003 | Hogan | |
| 6,581,606 B2 | 6/2003 | Kutzko et al. | |
| 6,671,563 B1 | 12/2003 | Engelson et al. | |
| 6,745,764 B2 | 6/2004 | Hickle | |
| 6,757,898 B1 | 6/2004 | Ilsen et al. | |
| 6,785,589 B2 | 8/2004 | Eggenberger et al. | |
| 6,796,956 B2 | 9/2004 | Hartlaub et al. | |
| 6,799,149 B2 | 9/2004 | Hartlaub | |
| 6,847,861 B2 | 1/2005 | Lunak et al. | |
| 6,856,247 B1 | 2/2005 | Wallace | |
| 6,993,402 B2 | 1/2006 | Klass et al. | |
| 7,034,691 B1 | 4/2006 | Rapaport et al. | |
| 7,054,844 B2 | 5/2006 | Fletcher et al. | |
| 7,096,072 B2 | 8/2006 | Engleson et al. | |
| 7,215,991 B2 | 5/2007 | Besson et al. | |
| 7,229,430 B2 | 6/2007 | Hickle et al. | |
| 7,230,529 B2 | 6/2007 | Ketcherside, Jr. et al. | |
| 7,256,708 B2 | 8/2007 | Rosenfeld et al. | |
| 7,263,492 B1 | 8/2007 | Suresh et al. | |
| 7,379,885 B1 | 5/2008 | Zakim | |
| 7,384,420 B2 | 6/2008 | Dycus et al. | |
| 7,421,709 B2 | 9/2008 | Watson et al. | |
| 7,433,853 B2 | 10/2008 | Brockway et al. | |
| 7,471,994 B2 | 12/2008 | Ford et al. | |
| 7,526,769 B2 | 4/2009 | Watts, Jr. et al. | |
| 7,587,415 B2 | 9/2009 | Gaurav et al. | |
| 7,612,679 B1 | 11/2009 | Fackler et al. | |
| 7,693,697 B2 | 4/2010 | Westenskow et al. | |
| 7,769,601 B1 | 8/2010 | Bleser et al. | |
| 7,771,385 B2 | 8/2010 | Eggers et al. | |

(56) References Cited

U.S. PATENT DOCUMENTS

| | | |
|---|---|---|
| 7,771,386 B2 | 8/2010 | Eggers et al. |
| 7,787,946 B2 | 8/2010 | Stahmann et al. |
| 7,796,045 B2 | 9/2010 | Spear et al. |
| 7,835,927 B2 | 11/2010 | Schlotterbeck et al. |
| 7,860,583 B2 | 12/2010 | Condurso et al. |
| 7,962,544 B2 | 6/2011 | Torok et al. |
| 7,970,550 B2 | 6/2011 | Arakelyan et al. |
| 8,005,688 B2 | 8/2011 | Coffman et al. |
| 8,024,200 B2 | 9/2011 | Jennings et al. |
| 8,160,895 B2 | 4/2012 | Schmitt et al. |
| 8,197,437 B2 | 6/2012 | Kalafut et al. |
| 8,291,337 B2 | 10/2012 | Gannin et al. |
| 8,340,792 B2 | 12/2012 | Condurso et al. |
| 2001/0037083 A1 | 11/2001 | Hartlaub et al. |
| 2001/0044731 A1 | 11/2001 | Coffman et al. |
| 2002/0016568 A1 | 2/2002 | Lebel et al. |
| 2002/0022973 A1 | 2/2002 | Sun et al. |
| 2002/0026223 A1 | 2/2002 | Riff et al. |
| 2002/0033548 A1 | 3/2002 | Brodkin et al. |
| 2002/0035484 A1 | 3/2002 | McCormick |
| 2002/0038392 A1 | 3/2002 | De La Huerga |
| 2002/0042636 A1 | 4/2002 | Koshiol et al. |
| 2002/0077849 A1 | 6/2002 | Baruch et al. |
| 2002/0087114 A1 | 7/2002 | Hartlaub |
| 2002/0116509 A1 | 8/2002 | DeLaHuerga |
| 2002/0120350 A1* | 8/2002 | Klass et al. ............ 700/1 |
| 2002/0169636 A1 | 11/2002 | Eggers et al. |
| 2002/0198624 A1 | 12/2002 | Greenwald et al. |
| 2003/0009244 A1 | 1/2003 | Engleson et al. |
| 2003/0036683 A1 | 2/2003 | Kehr et al. |
| 2003/0045858 A1* | 3/2003 | Struys et al. ............ 604/503 |
| 2003/0051737 A1 | 3/2003 | Hickle et al. |
| 2003/0063524 A1 | 4/2003 | Niemiec et al. |
| 2003/0069481 A1 | 4/2003 | Hervy et al. |
| 2003/0105389 A1 | 6/2003 | Noonan et al. |
| 2003/0105555 A1 | 6/2003 | Lunak et al. |
| 2003/0106553 A1 | 6/2003 | Vanderveen |
| 2003/0114836 A1 | 6/2003 | Estes et al. |
| 2003/0129578 A1 | 7/2003 | Mault |
| 2003/0135087 A1* | 7/2003 | Hickle et al. ............ 600/26 |
| 2003/0135388 A1 | 7/2003 | Martucci et al. |
| 2003/0139701 A1 | 7/2003 | White et al. |
| 2003/0140928 A1 | 7/2003 | Bui et al. |
| 2003/0140929 A1 | 7/2003 | Wilkes et al. |
| 2003/0149599 A1 | 8/2003 | Goodall et al. |
| 2003/0156143 A1 | 8/2003 | Westenskow et al. |
| 2003/0163223 A1 | 8/2003 | Blomquist |
| 2003/0205897 A1 | 11/2003 | Kaufman |
| 2003/0236683 A1 | 12/2003 | Henderson et al. |
| 2004/0068229 A1 | 4/2004 | Jansen et al. |
| 2004/0073329 A1 | 4/2004 | Engleson et al. |
| 2004/0128162 A1 | 7/2004 | Schlotterbeck et al. |
| 2004/0152622 A1 | 8/2004 | Keith et al. |
| 2004/0167465 A1 | 8/2004 | Mihai et al. |
| 2004/0167804 A1 | 8/2004 | Simpson et al. |
| 2004/0172283 A1 | 9/2004 | Vanderveen et al. |
| 2004/0172302 A1 | 9/2004 | Martucci et al. |
| 2004/0176297 A1 | 9/2004 | Cheung et al. |
| 2004/0188998 A1 | 9/2004 | Henthorn |
| 2004/0193325 A1 | 9/2004 | Bonderud et al. |
| 2004/0193446 A1 | 9/2004 | Mayer et al. |
| 2004/0260478 A1 | 12/2004 | Schwamm |
| 2005/0010166 A1* | 1/2005 | Hickle ............ 604/66 |
| 2005/0020996 A1 | 1/2005 | Hartlaub et al. |
| 2005/0021297 A1 | 1/2005 | Hartlaub |
| 2005/0033606 A1 | 2/2005 | Miller |
| 2005/0049179 A1* | 3/2005 | Davidson et al. ............ 514/3 |
| 2005/0055242 A1 | 3/2005 | Bello et al. |
| 2005/0096941 A1 | 5/2005 | Tong |
| 2005/0097566 A1 | 5/2005 | Watts et al. |
| 2005/0107914 A1 | 5/2005 | Engleson et al. |
| 2005/0108057 A1 | 5/2005 | Cohen et al. |
| 2005/0113945 A1 | 5/2005 | Engleson et al. |
| 2005/0119788 A1* | 6/2005 | Engleson et al. ............ 700/231 |
| 2005/0144043 A1 | 6/2005 | Holland et al. |
| 2005/0145010 A1 | 7/2005 | Vanderveen et al. |
| 2005/0171815 A1 | 8/2005 | Vanderveen |
| 2005/0224083 A1 | 10/2005 | Crass et al. |
| 2005/0278194 A1* | 12/2005 | Holland et al. ............ 705/2 |
| 2006/0026205 A1 | 2/2006 | Butterfield |
| 2006/0047538 A1 | 3/2006 | Condurso et al. |
| 2006/0053036 A1 | 3/2006 | Coffman et al. |
| 2006/0190302 A1 | 8/2006 | Eggers et al. |
| 2006/0200369 A1 | 9/2006 | Batch et al. |
| 2006/0206356 A1 | 9/2006 | Vanderveen |
| 2006/0217628 A1 | 9/2006 | Huiku |
| 2006/0218015 A1 | 9/2006 | Walker et al. |
| 2006/0249423 A1 | 11/2006 | Reijonen |
| 2006/0271401 A1 | 11/2006 | Lassetter et al. |
| 2007/0015972 A1 | 1/2007 | Wang et al. |
| 2007/0043767 A1 | 2/2007 | Osborne et al. |
| 2007/0061393 A1 | 3/2007 | Moore |
| 2007/0083389 A1 | 4/2007 | Dyer et al. |
| 2007/0106457 A1 | 5/2007 | Rosenberg |
| 2007/0106753 A1 | 5/2007 | Moore |
| 2007/0106754 A1 | 5/2007 | Moore |
| 2007/0156860 A1 | 7/2007 | Nedelcu et al. |
| 2007/0168301 A1 | 7/2007 | Eisner et al. |
| 2007/0208454 A1 | 9/2007 | Forrester et al. |
| 2007/0210157 A1 | 9/2007 | Miller |
| 2007/0293843 A1 | 12/2007 | Ireland et al. |
| 2008/0025230 A1 | 1/2008 | Patel et al. |
| 2008/0034323 A1 | 2/2008 | Blomquist |
| 2008/0141272 A1 | 6/2008 | Borgendale et al. |
| 2008/0164998 A1 | 7/2008 | Scherpbier et al. |
| 2008/0169045 A1 | 7/2008 | Tribble et al. |
| 2008/0195246 A1 | 8/2008 | Tribble et al. |
| 2008/0272138 A1 | 11/2008 | Ross et al. |
| 2008/0317672 A1 | 12/2008 | Viertio-Oja |
| 2009/0012812 A1 | 1/2009 | Rausch et al. |
| 2009/0012813 A1 | 1/2009 | Berzansky et al. |
| 2009/0099867 A1 | 4/2009 | Newman |
| 2009/0112333 A1 | 4/2009 | Sahai |
| 2009/0150484 A1 | 6/2009 | Roberts |
| 2009/0240651 A1 | 9/2009 | Fletcher et al. |
| 2009/0306585 A1 | 12/2009 | Pang et al. |
| 2009/0306944 A1 | 12/2009 | Willmann et al. |
| 2010/0094653 A1 | 4/2010 | Tribble et al. |
| 2010/0161113 A1 | 6/2010 | Tribble et al. |
| 2010/0169120 A1 | 7/2010 | Herbst et al. |
| 2010/0169771 A1 | 7/2010 | Pelegrin et al. |
| 2010/0174552 A1 | 7/2010 | Hawkes et al. |
| 2010/0174553 A1 | 7/2010 | Kaufman et al. |
| 2010/0179825 A1 | 7/2010 | Hanov et al. |
| 2010/0241453 A1 | 9/2010 | Malec |
| 2010/0271218 A1 | 10/2010 | Hoag et al. |
| 2010/0280840 A1 | 11/2010 | Fukushi et al. |
| 2010/0323397 A1 | 12/2010 | Reavy et al. |
| 2011/0046975 A1 | 2/2011 | Hoffman |
| 2011/0060758 A1 | 3/2011 | Schlotterbeck et al. |
| 2011/0119612 A1 | 5/2011 | Gannon et al. |
| 2011/0288882 A1 | 11/2011 | Halow |
| 2012/0011253 A1 | 1/2012 | Friedman et al. |
| 2012/0016215 A1 | 1/2012 | Condurso et al. |
| 2012/0053533 A1 | 3/2012 | Butterfield et al. |
| 2012/0075061 A1 | 3/2012 | Barnes |
| 2012/0136673 A1 | 5/2012 | Presley et al. |
| 2012/0173264 A1 | 7/2012 | Brush et al. |
| 2012/0239824 A1 | 9/2012 | Nguyen et al. |
| 2012/0247480 A1 | 10/2012 | Varga |
| 2012/0253835 A1 | 10/2012 | Tracy et al. |
| 2012/0265549 A1 | 10/2012 | Virolainen |
| 2013/0018356 A1 | 1/2013 | Prince et al. |
| 2013/0096444 A1 | 4/2013 | Condurso et al. |
| 2013/0197927 A1 | 8/2013 | Vanderveen et al. |
| 2013/0197928 A1 | 8/2013 | Vanderveen et al. |
| 2013/0197929 A1 | 8/2013 | Vanderveen et al. |
| 2013/0197930 A1 | 8/2013 | Garibaldi et al. |
| 2013/0197931 A1 | 8/2013 | Gupta et al. |
| 2013/0204433 A1 | 8/2013 | Gupta et al. |
| 2013/0204637 A1 | 8/2013 | Vanderveen et al. |
| 2013/0262138 A1 | 10/2013 | Jaskela et al. |

(56) References Cited

U.S. PATENT DOCUMENTS

| | | |
|---|---|---|
| 2014/0028464 A1 | 1/2014 | Garibaldi |
| 2014/0100868 A1 | 4/2014 | Condurso et al. |
| 2014/0297313 A1 | 10/2014 | Condurso et al. |

FOREIGN PATENT DOCUMENTS

| | | |
|---|---|---|
| EP | 0192786 A2 | 9/1986 |
| EP | 0384155 A2 | 8/1990 |
| EP | 0595474 A2 | 5/1994 |
| EP | 0649316 A1 | 4/1995 |
| EP | 0652528 A2 | 5/1995 |
| EP | 0784283 A1 | 7/1997 |
| EP | 0921488 A1 | 6/1999 |
| EP | 1003121 A2 | 5/2000 |
| EP | 1018347 A2 | 7/2000 |
| EP | 1237113 A2 | 9/2002 |
| GB | 2 141 006 A | 12/1984 |
| JP | S62114562 | 5/1987 |
| JP | H11505352 | 5/1999 |
| JP | 2002520718 A | 7/2002 |
| JP | 2003085283 A | 3/2003 |
| JP | 2004287616 A | 10/2004 |
| JP | 2006155070 A | 6/2006 |
| JP | H5168708 B2 | 3/2013 |
| KR | 1020070045611 A | 5/2007 |
| KR | 1020080013129 A | 2/2008 |
| KR | 100847397 B1 | 7/2008 |
| KR | 1020100125972 A | 12/2010 |
| KR | 20110070824 A | 6/2011 |
| KR | 1020120076615 A | 7/2012 |
| KR | 1020120076635 A | 7/2012 |
| NZ | 522631 A | 7/2004 |
| WO | WO-9322735 A1 | 11/1993 |
| WO | WO-9405344 A1 | 3/1994 |
| WO | WO-9408647 A1 | 4/1994 |
| WO | WO-9413250 A1 | 6/1994 |
| WO | WO-9523378 A2 | 8/1995 |
| WO | WO-9620745 A1 | 7/1996 |
| WO | WO-9625214 A1 | 8/1996 |
| WO | WO-9636923 A1 | 11/1996 |
| WO | WO-9704712 A1 | 2/1997 |
| WO | WO-9813783 A1 | 4/1998 |
| WO | WO-9828676 A2 | 7/1998 |
| WO | WO-9909505 A1 | 2/1999 |
| WO | WO-9910829 A1 | 3/1999 |
| WO | WO-9910830 A1 | 3/1999 |
| WO | WO-9935588 A1 | 7/1999 |
| WO | WO-9944167 A1 | 9/1999 |
| WO | WO-9945490 A2 | 9/1999 |
| WO | WO-9946718 A1 | 9/1999 |
| WO | WO-9967732 A1 | 12/1999 |
| WO | WO-0003344 | 1/2000 |
| WO | WO-0004521 | 1/2000 |
| WO | WO-0018449 | 4/2000 |
| WO | WO-0032088 | 6/2000 |
| WO | WO-0032098 | 6/2000 |
| WO | WO-0186506 | 11/2001 |
| WO | WO-0188828 | 11/2001 |
| WO | WO-0236044 | 5/2002 |
| WO | WO-02069099 | 9/2002 |
| WO | WO-03038566 | 5/2003 |
| WO | WO-03053503 | 7/2003 |
| WO | WO-03092769 | 11/2003 |
| WO | WO-03094091 | 11/2003 |
| WO | WO-2004060443 A2 | 7/2004 |
| WO | WO-2004061745 A2 | 7/2004 |
| WO | WO-2010124016 A1 | 10/2010 |
| WO | WO-2010124328 A1 | 11/2010 |

OTHER PUBLICATIONS

U.S. Appl. No. 13/901,501, filed May 23, 2013.
Non-Final Office Action dated Oct. 24, 2014, issued in U.S. Appl. No. 13/559,537.
International Search Reports and Written Opinions of the International Searching Authority dated Jun. 18, 2014 and Jun. 19, 2014 for PCT applications PCT/US2014/022830, PCT/US2014/022835 and PCT/US2014/022837. Office Action issued in U.S. Appl. Nos. 13/802,683, dated Apr. 29, 2014, 13/802,446, dated Aug. 13, 2014, 09/860,865 dated Jul. 25, 2014 and 13/802,433 dated Aug. 25, 2014.
International Search Reports and Written Opinions of the International Searching Authority dated Jun. 19, 2014 and Jun. 24, 2014 for PCT Application Nos. PCT/US2014/022840 and PCT/US2014/022832.
U.S. Appl. No. 90/009,912, filed Aug. 12, 2013, Schlotterbeck et al.
U.S. Appl. No. 90/011,697, filed Aug. 12, 2013, Schlotterbeck et al.
"General-Purpose Infusion Pumps," Evaluation—Health Devices, Oct. 2002, pp. 353-387, vol. 31 (10), ECRI Institute.
"Infusion Pump Technology," Health Devices, Apr.-May 1998, pp. 150-170, vol. 27(4-5), ECRI Institute.
"Infusion Pumps, General Purpose," Healthcare Product Comparison System, 2007, pp. 1-54, ECRI Institute.
"Infusion Pumps, Large-Volume," Healthcare Product Comparison System, 2010, pp. 1-51, ECRI Institute.
"Smart Infusion Pumps Join CPOE and Bar Coding as Important Ways to Prevent Medication Errors," ISMP—Medication Safety Alert, Feb. 7, 2002, 2 pgs., Institute for Safe Medication Practices.
Anonymous, Guardrails®Safety Software—MedleyTM Medication Safety System, Alaris Medical Systems XP-00234431; 2002 Alaris Medical Systems Inc. Nov. 2002, SSM @2159C.
Baldauf-Sobez et al., "How Siemens' Computerized Physician Order Entry Helps Prevent the Human Errors," electromedica, vol. 71, No. 1, 2003, pp. 2-10.
Eskew, James et al., Using Innovative Technologies to Set New Safety Standards for the Infusion of Intravenous Medications, Hospital Pharmacy, vol. 37, No. 11, pp. 1179-1189, 2002, Facts and Comparisons.
Kohn, et al., "To Err is Human—Building a Safer Health System," National Academy Press, 2002, pp. i-287, National Academy of Sciences.
Lesar, "Recommendations for Reducing Medication Errors," Medscape Pharmacists, posted Jul. 24, 2000, 10 pgs, vol. 1(2), Medscape Pharmacists, <http://www.medscape.com>.
Meier, "Hospital Products Get Seal of Approval at a Price," The New York Times, Apr. 23, 2002, 5 pgs.
Queensland Health. Use of returned or unused dispensed medicines, Jan. 5, 2005, Queensland Government. pp. 1-2.
Shabot et al., "Wireless clinical alerts for critical medication, laboratory and physiologic data," System Sciences 2000. Proceedings of the 33rd Annual Conference on Jan. 4-7, 2000, Piscataway, NJ, IEEE, Jan. 4, 2000.
Williams, et al., "Reducing the Risk of User Error with Infusion Pumps," Professional Nurse—Safe Practice—Infusion Devices, Mar. 2000, pp. 382-384, vol. 15(6).
Yokoi, "Prevention of Errors in Injection/Drip Infusion—No excuse for ignorance! —Essential Points of Accident Prevention, IV Infusion Pump, Syringe-pump Accident Prevention," JIN Special, Igaku Shoin K.K., Dec. 1, 2001, pp. 109-120, No. 70.

* cited by examiner

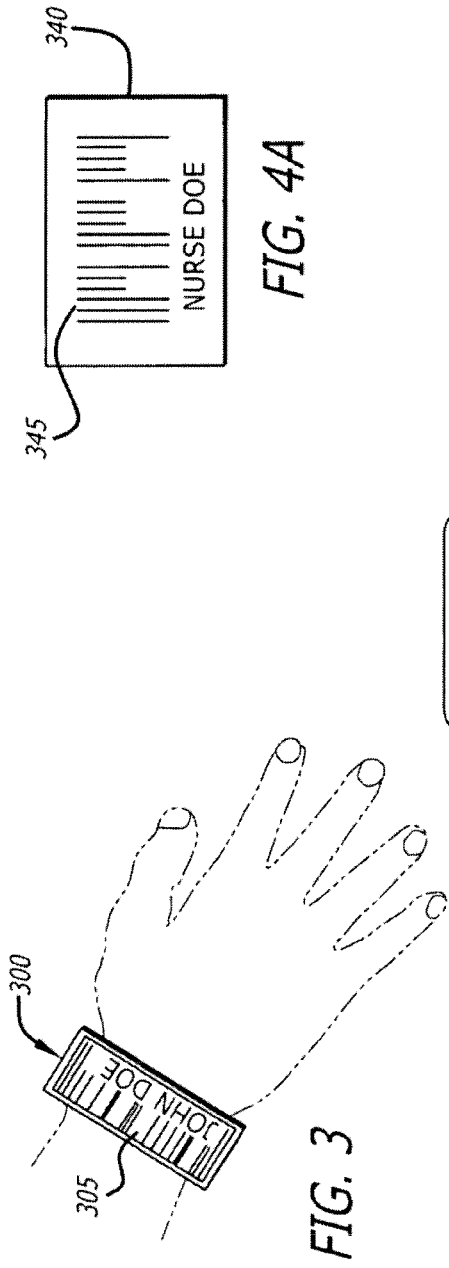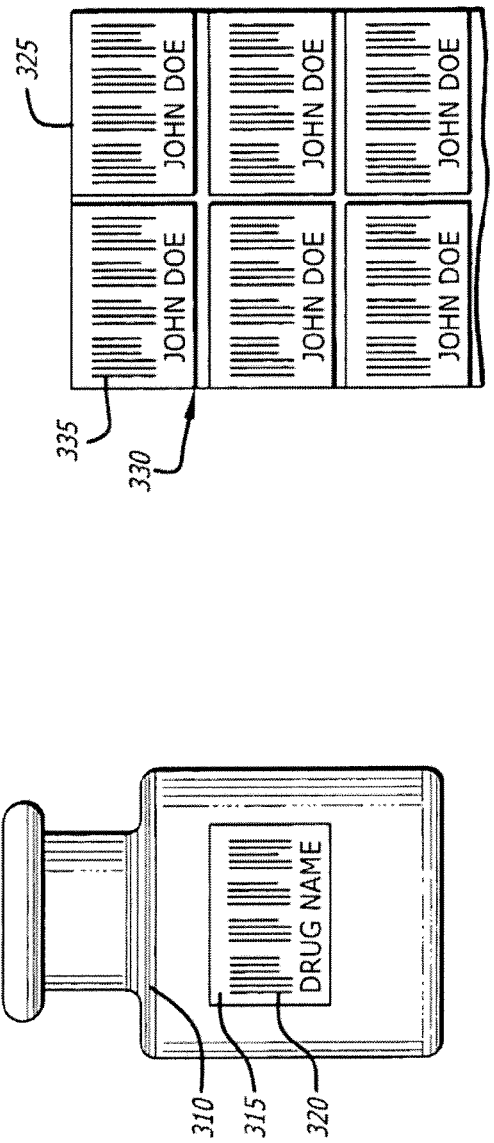

SYSTEM AND METHOD FOR DYNAMICALLY ADJUSTING PATIENT THERAPY

CROSS-REFERENCE TO RELATED APPLICATIONS

The present application is a continuation of U.S. patent application Ser. No. 14/103,816, filed Dec. 11, 2013, entitled "System and Method for Dynamically Adjusting Patient Therapy," which is a continuation of U.S. patent application Ser. No. 13/705,032, filed Dec. 4, 2012, now U.S. Pat. No. 8,630,722, entitled "System and Method for Dynamically Adjusting Patient Therapy," which is a continuation of U.S. patent application Ser. No. 12/947,773, filed Nov. 16, 2010, now U.S. Pat. No. 8,340,792, entitled "System and Method for Dynamically Adjusting Patient Therapy," which is a continuation of U.S. patent application Ser. No. 10/925,511, filed Aug. 25, 2004, now U.S. Pat. No. 7,860,583, entitled "System and Method for Dynamically Adjusting Patient Therapy." The entire disclosures of each of the above patent applications and patents are hereby incorporated by reference, for all purposes.

FIELD OF THE INVENTION

The present invention relates generally to systems and methods for managing patient care in a health care facility, and more particularly, to systems and methods for monitoring the therapy delivered to a patient, comparing the therapy administered, and the progress of the patient to guidelines based upon information obtained from sensors associated with the patient, laboratory and clinical measurements, institution best practices, patient parameters and requirements, and adjusting the therapy delivered to the patient depending on the outcome of the comparison by providing control signals to medical devices tasked with delivery of the therapy to the patient.

BACKGROUND OF THE INVENTION

Until recently, the delivery of therapeutic treatment to a patient has been essentially a manual operation. Treatment orders were hand written, or telephoned to a pharmacy or care giver. The treatment modalities, such as drugs, either in orally ingestible form or in the form of infusion fluid, topical, injectable, or in drop form, were carried to the location of the patient and manually administered. In the case of infusion fluids, the bags and fluid delivery sets were set into an infusion pump, and a nurse entered various operational parameters into the pump to initiate the infusion. Records of the medication or therapy administration were essentially hand written, even where they were eventually logged into a computer database. Because of the manual nature of the system, errors in delivery therapy to the patient were not uncommon.

Medication errors, that is, errors that occur in the ordering, dispensing, and administration of medications, regardless of whether those errors caused injury or not, are a significant consideration in the delivery of healthcare in the institutional setting. Adverse drug events ("ADE"), defined as injuries involving a drug that require medical intervention, and representing some of the most serious medication errors, are responsible for a number of patient injuries and death. Accordingly, healthcare facilities continually search for ways to reduce the occurrence of medication errors.

Various systems and methods are being developed at present to reduce the frequency of occurrence and severity of preventable adverse drug events ("PADE") and other medication errors. In the administration of medication, focus is typically directed to the following five "rights" or factors: the right patient, the right drug, the right route, the right amount, and the right time. Systems and methods seeking to reduce ADE's and PADE's should take these five rights into consideration.

In many hospitals and clinical laboratories, a bracelet device having the patient's identification, such as his or her name printed thereon, is affixed to a patient upon admittance to the facility in order to identify the patient during his or her entire stay. Despite this safeguard, opportunities arise for patient identification error. For example, when a blood sample is taken from a patient, the blood sample must be identified by manually transcribing the patient's name and other information from the patient's identification bracelet. In transferring the patient's name, a nurse or technician may miscopy the name or may rely on memory or a different data source. Moreover, manually transferring other information such as parameters for configuring an infusion pump to dispense medication may result in errors that reduce the accuracy and/or effectiveness of drug administration and patient care. This may result in an increased duration of treatment with an attendant increase in cost.

Hospitals and other healthcare institutions continuously strive to provide quality patient care. The possibility of medical errors, such as where the wrong patient receives the wrong drug at the wrong time, in the wrong dosage, or even where the wrong surgery is performed, is a significant concern for all healthcare facilities. Many prescription drugs and injections are identified merely by slips of paper on which the patient's name and identification number have been hand-written by a nurse or technician who is to administer the treatment. For a variety of reasons, such as the transfer of patients to different beds and errors in marking the slips of paper, the possibility arises that a patient may be given an incorrect treatment. This could be prevented by using an automated system to verify that the patient is receiving the correct care. Various solutions to these problems have been proposed, such as systems that use bar codes to identify patients and medications, or systems allowing the bedside entry of patient data. While these systems have advanced the art significantly, even more comprehensive systems could prove to be of greater value.

Errors can occur during the prescribing, transcribing, dispensing and/or administering phases of the medication process. In a typical facility, a physician enters an order for a medication for a particular patient. This order may be handled either as a simple prescription slip, or it may be entered into an automated system, such as a computerized physician order entry ("CPOE") system. The prescription slip or the electronic prescription from the CPOE system is routed to the pharmacy, where the order is filled, so that the medication can be provided to the patient. Typically, pharmacies check the physician order against possible allergies of the patient and for possible drug interactions in the case where two or more drugs are prescribed, and also check for contraindications. Depending on the facility, the medication may be identified and gathered within the pharmacy and placed into a transport carrier for transport to a nurse station. Once at the nurse station, the prescriptions are again checked against the medications that have been identified for delivery to ensure that no errors have occurred.

Typically, medications are delivered to a nurse station in a drug cart or other carrier that allows a certain degree of security to prevent theft or other loss of medications. In one example, the drug cart or carrier is divided into a series of drawers or containers, each container holding the prescribed medication for a single patient. To access the medication, the nurse must enter the appropriate identification to unlock a drawer, door, or container. In other situations, inventories of commonly-used drugs may be placed in a secure cabinet located in an area at or close by a nurse station. This inventory may contain not only topical medications but oral, intramuscular-(IM), and intravenous (IV)-delivered medications as well. Nurse identification and a medication order number are sometimes required to gain access to the cabinet.

The nurse station receives a listing of drugs to be delivered to patients at intervals throughout the day. A nurse or other qualified person refers to the list of medications to be delivered, and obtains those medications from the inventory at the nurse station or medication room. The medications are then taken to the individual patients and the doses are administered.

Common to all of these systems is the nurse who delivers the medication. The nurse is central to the process of verifying that the right medication is given to the right patient in the right dosage at the right time at the point of care. No other person in the facility is situated as well as the nurse delivering the medication to ensure or verify that the appropriate drug is being given to the appropriate patient.

Such a system though may not be capable of thoroughly verifying that the appropriate medication regimen is being delivered to a patient in the case where IV drugs are being delivered. For example, a nurse may carry an IV bag to a particular patient area, hang the bag, program an infusion pump with appropriate treatment parameters, and begin infusion of the medication. The applicable hospital control system, such as the pharmacy information system, may not be informed that the patient has received the medication, such as when a verbal order has not yet been entered into the system, and if the information is lost somewhere, the possibility exists of medicating the patient twice. Thus, there may be a break in the link of verification that the medication is being properly delivered to the patient if an event occurs resulting in a deviation from the desired treatment parameters.

Moreover, even where the right medication arrives at the right patient for administration, incorrect administration of the medication may occur where the medication is to be administered using an automated or semi-automated administration device, such as an infusion pump, ii the automated device is programmed with incorrect medication administration parameters. For example, even where the medication order includes the correct infusion parameters, those parameters may be incorrectly entered into an infusion pump, causing the infusion pump to administer the medication in a manner that may not result in the prescribed treatment.

One attempt at providing an infusion system with built-in safeguards to prevent the incorrect entry of treatment parameters utilizes hospital-defined drug dosing parameters which are employed by the infusion instrument's software to monitor the infusion parameter entry process and interact with the care-giver should an incorrect entry or an out of range entry be attempted. In such a case, an alert is communicated to the care-giver that the parameter entered is either incorrect or outside of a range established by the institution where care is being provided. The drug dosing parameters consist of hospital-defined values for infusion parameters or other medical treatment guidelines. They may comprise the considered "best practices" of the facility and may be updated from time to time.

In some cases, diverse types or models of patient care devices may need to communicate with each other for purposes of sharing information. For instance, patient monitoring devices such as vital signs monitors often have the capability of storing transactions from other patient care devices, such as infusion pumps. These monitoring devices typically require the parameters of the other patient care devices so that appropriate correlation, labeling, data validation and storage functions may be provided. Additionally, in cases where the drug dosing parameters further include rule sets representing patient-condition-specific rules and/or algorithms that determine dosing parameter(s) as a function of patient data obtained from other sources in the network, information from one device may be essential to another device that is utilizing the hospital's drug dosing parameters. Further, some devices may alter operation in response to the information received from another device, either in accordance with a drug dosing rule or other operational software in the system or device. For example, the rule for maximum and minimum dose of a vasoactive drug such as sodium nitroprusside can be made dependent on the arterial blood pressure measured by a separate instrument. If the mean blood pressure exceeds a predetermined limit or meets a certain categorization such as "high", then the dosing parameter defining the upper continuous dose limit would be reduced in accordance with the parameters of the dosing rule for that drug within a selected behavior descriptor, as that term will be defined below.

However, each healthcare facility typically has a different inventory of diverse models of patient care devices, many of which are not compatible with each other because they are made by different manufacturers or are otherwise supported by different platforms that use different languages and/or communication protocols to transmit or receive data. Thus, it would be advantageous to provide a universal configuration database from which these diverse devices could easily obtain the needed communication information (e.g. data definitions, rules, protocols, data structures and the like) to support communication with other types of patient care devices. It would also be advantageous if such a system was integrated with the customizable drug dosing parameters and rules as well as the infusion/monitoring instrument's operational configuration parameters.

The operational behavior of many infusion devices are capable of being customized through installation of "configurable operation parameters" including such parameters as alarm limits, maximum rates, selection of operational modes and languages. Depending on the type of infusion device and area in which the device is used, specific settings are needed to provide optimal care. For instance, the neonatology department will prefer a low rate limit, the smallest air bubble detection limit and special settings for pressure and resistance alarms.

For example, many infusion pumps presently available allow users to determine the behavior of the medical device by choosing one of a list of behaviors referred to as "profiles." The parameters of each "profile" are defined generically as behavior descriptors, the elements of which are selected to provide optimal behavior of the medical device in a specific care area (ICU, OR, etc.) or type of medical care (cardiology, oncology). By the operator's selection of a "profile", the infusion pump or other medical device becomes automatically customized to provide optimal operating features for the patient's in the selected care area. For example, both infusion devices and vital signs monitoring modules may be combined in a single integrated patient care system controlled by a central computer referred to as a PCU ("point-of-care unit"). The operational behaviors of monitoring modules include features such as alarm limits and display range. Similar to infusion modules, the behavior of these devices may be customized through the selection of the desired "profile" or ensemble of operating parameters.

What has been needed, and heretofore unavailable, is an integrated system deployable within an institution that ties together the various prescribing, delivering, and reporting processes that deliver therapy to a patient. Moreover, such a system would be able to access a database or databases of various rules and patient information, including institution medical records, clinical records and data, such as the information provided by various clinical devices, such as blood pressure monitors, $PCO_2$ monitors, glucose monitors, etc., and laboratory equipment, such as that used in blood analysis and the like, and use the accessed information to alter the therapy provided to the patient as appropriate to ensure that the outcome of the therapy, that is, the health of the patient, is optimized. Such a system would also include reporting capabilities to allow for monitoring and recording of the therapy delivered to a patient, including the ability to create or update a medical administration record, and store the record on a server where it is available to personnel and institutional systems that need access to it. In addition, the rules and guidelines used to assess the delivery of a therapy to a patient would be flexible and capable of being dynamically adjusted as therapy is delivered to the patient so that corrections to the therapy may be made to optimize the outcome of the therapy. Such a system should also be capable of facilitating communication between heterogeneous patient care devices for further integrating the various aspects of patient care such as the operational parameters of infusion devices and monitors. The invention fulfills these needs and others.

SUMMARY OF THE INVENTION

Briefly, and in general terms, the present invention is directed to a new and improved information management system and method capable of creating, managing and controlling a hospital-defined universal configuration database for patient care devices at a healthcare facility.

In one aspect, the present invention comprises a system for managing therapy provided to a patient, comprising: a communication system, the communication system configured to provide two way transmission of information over the communication system, a medication delivery device having a processor and a memory associated with the processor for storing programs for operating the processor to control the medication delivery device, the medication delivery device also including a communication means, an input device for inputting patient and drug information, and a display, all in operable communication with the processor, the medication delivery device capable of communicating over the communication system through its communication means, at least one server operably connected to the communication system, the at least one server configured to access a database representative of at least one institutionally determined rule, and also configured to monitor activity of the medication delivery device and provide the medication delivery device with patient and drug information and operating commands, wherein information entered into the medication delivery device using the input device is communicated to the server and the server compares the communicated information to information stored in the database of at least one institutionally determined rule to determine if the communicated information falls within a range of values indicated as acceptable by the at least one institutionally determined rule, and wherein if the comparison indicates that the communicated information does not fall within a range of values indicated as acceptable; the at least one server provides an alert to a caregiver.

In another aspect, the server of the present invention monitors a status of the alert, and if a selected period of time elapses without a change in the status of the alert, increases a priority of the alert. In an alternate aspect, the server transmits the alert with the increased priority to a care giver through the communication system. In yet another aspect, the server monitors information communicated through the communication system to determine if a required laboratory or other test for a patient has been performed within a selected period of time, and wherein if the test has not been performed, communicates an alert to a care giver. Alternatively, the server monitors a status of the alert, and if a selected period of time elapses without a change in the status of the alert, increases a priority of the alert and communicates the alert with the increased priority to the caregiver. In still another alternative, the server monitors a status of the alert with the increased priority, and if a selected period of time elapse without a change in the status of the alert with the increased priority, communicates an alert with a further increase of priority to the care giver, and in another aspect, the server also communicates a command to the processor of the medication delivery device to stop delivery of the medication.

In a still further aspect, the server of the present invention stores records containing information related to the alert in a memory, and wherein the server analyzes the stored records and generates reports of the information related to the alerts.

In yet another aspect, at least one institutionally determined rule stored on the database of the system of the present invention is a pharmacokinetic model. In one alternative, the at least one institutionally determined rule is a pharmacodynamic model, while in another alternative, at least one institutionally determined rule contains information related to drug incompatibilities.

In still another aspect, the medication delivery device of the present invention is an infusion pump and the processor monitors medication identification information entered by the input device and compares the entered information with medication identification information of a medication already being infused by the pump and accesses the drug incompatibility information stored on the server and, if the comparison indicates that entered medication is incompatible with the infusing medication, the processor communicates an alert to the care giver. In yet another aspect, the processor accesses the server and retrieves at least one recommendation for altering a prescribed treatment regimen and communicates the at least one recommendation to the care giver.

In another aspect, the present invention includes a method of managing patient therapy, comprising: communicating information between therapy delivery devices, monitoring devices and institutional information systems; monitoring information communicated between the therapy delivery devices, monitoring devices and institutional information systems; comparing the communicated information with a database of institutionally determined rules related to therapies to be delivered to patients in an institution; identifying instances when a proposed therapy to be delivered to a patient violates at least one rule of the database of institutionally determined rules; and communicating an alert to a care giver that the proposed therapy violates the at least one rule.

In a further aspect, the method of the present invention further comprises monitoring the information communicated between the therapy delivery devices, monitoring devices and institutional information systems for information related to a specific patient, and alerting the care giver if any of the monitored patient specific information violates the at least one rule of the database of institutionally determined rules. In one alternative aspect, monitoring the information includes monitoring for information generated by monitoring devices associated with the specific patient. In another alternative aspect, monitoring the information includes monitoring for information generated by laboratory or other tests associated with the specific patient; comparing the information generated by the laboratory or other test to the at least one rule; and alerting the care giver if the information generated by the laboratory or other test violates the at least one rule.

In a still further aspect, the method of the present invention further includes monitoring a status of the alert; increasing a priority of the alert if the monitored status of the alert indicates that the status of the alert has not changed within a selected period of time; and communicating the alert with the increased priority to the care giver. Alternatively, the method also includes providing the care giver with recommendations for resolving a cause of the alert, and in another alternative, the at least one rule includes information related to drug incompatibilities.

In yet a further aspect, the method of the present invention also comprises storing information related to a condition of the patient when the alert is communicated; storing information related to the therapy being delivered when the alert is communicated; and storing information related to the alert when the alert is communicated; analyzing the stored patient condition information, the therapy delivery information and the alert information; and reporting the analyzed information to the care giver. In another alternative aspect, the method further comprises providing recommendations for altering at least one rule in the database of institutionally determined rules in response to the analyzed information.

In yet another aspect, the present invention comprises a system for managing therapy provided to a patient, comprising: a communication system, the communication system configured to provide two way transmission of information over the communication system; a medication delivery device having a processor and a memory associated with the processor for storing programs for operating the processor to control the medication delivery device, the medication delivery device also including a communication means, an input device for inputting patient and drug information, and a display, all in operable communication with the processor, the medication delivery device capable of communicating over the communication system through its communication means; a second processor operably connected to the communication system, the second processor configured to access a database representative of at least one institutionally determined rule, and also configured to monitor activity of the medication delivery device and provide the medication delivery device with patient and drug information and operating commands; wherein information entered into the medication delivery device using the input device is communicated to the second processor and the second processor compares the communicated information to information stored in the database of at least one institutionally determined rule to determine if the communicated information falls within a range of values indicated as acceptable by the at least one institutionally determined rule; and wherein if the comparison indicates that the communicated information does not fall within a range of values indicated as acceptable; the second processor provides an alert to a caregiver. In one aspect, the database includes at least one rule related to drug incompatibility. In another aspect, the database includes at least one rule related to drug contra-indications.

In yet another aspect, the medication delivery device is an infusion pump. In still another aspect, the system further comprises a second infusion pump having a processor and a memory associated with the processor for storing programs for operating the processor to control the medication delivery device, the medication delivery device also including a communication means, an input device for inputting patient and drug information, and a display, all in operable communication with the processor, the medication delivery device capable of communicating over the communication system through its communication means to the second processor, and wherein the second processor monitors the activity of the second infusion pump, and compares the drugs being infused on the first and second infusion pumps to determine if the drugs are compatible.

In a still further aspect, the medication delivery device of the present invention further includes a means for notifying a caregiver of an alert, and wherein an alert provided by the second processor is also provided to the care giver by the means for notifying the care giver of the second infusion pump. And in a still further aspect, the database includes at least one rule pertaining to drug incompatibility, and the processor is programmed to compare a currently prescribed drug to at least one previously delivered drug to determine the presence of an incompatibility between the currently prescribed drugs and the at least one previously delivered drug.

Other features and advantages of the invention will become apparent from the following detailed description, taken in conjunction with the accompanying drawings, which illustrate, by way of example, the features of the invention.

BRIEF DESCRIPTION OF THE DRAWINGS

FIG. 3 is a graphic representation of a patient identification bracelet including a barcode that can be read by a barcode reader;

FIG. 4 depicts a barcode label affixed to a medication container that can be read by a barcode reader;

FIG. 4A shows a barcode label affixed to a care giver's identity badge;

FIG. 5 depicts a sheet of barcode labels that can be affixed to various containers or devices;

DETAILED DESCRIPTION OF THE INVENTION

The present invention provides a system and method for administering, monitoring and managing a patient's therapy in a healthcare facility according to the specifications of that facility. The present invention includes a variety of hardware, information databases and software programs that interact to gather, sort, store and provide reports to care givers at an institution regarding the delivery of medical care to a patent.

Digital Communication Network

Figure 1:
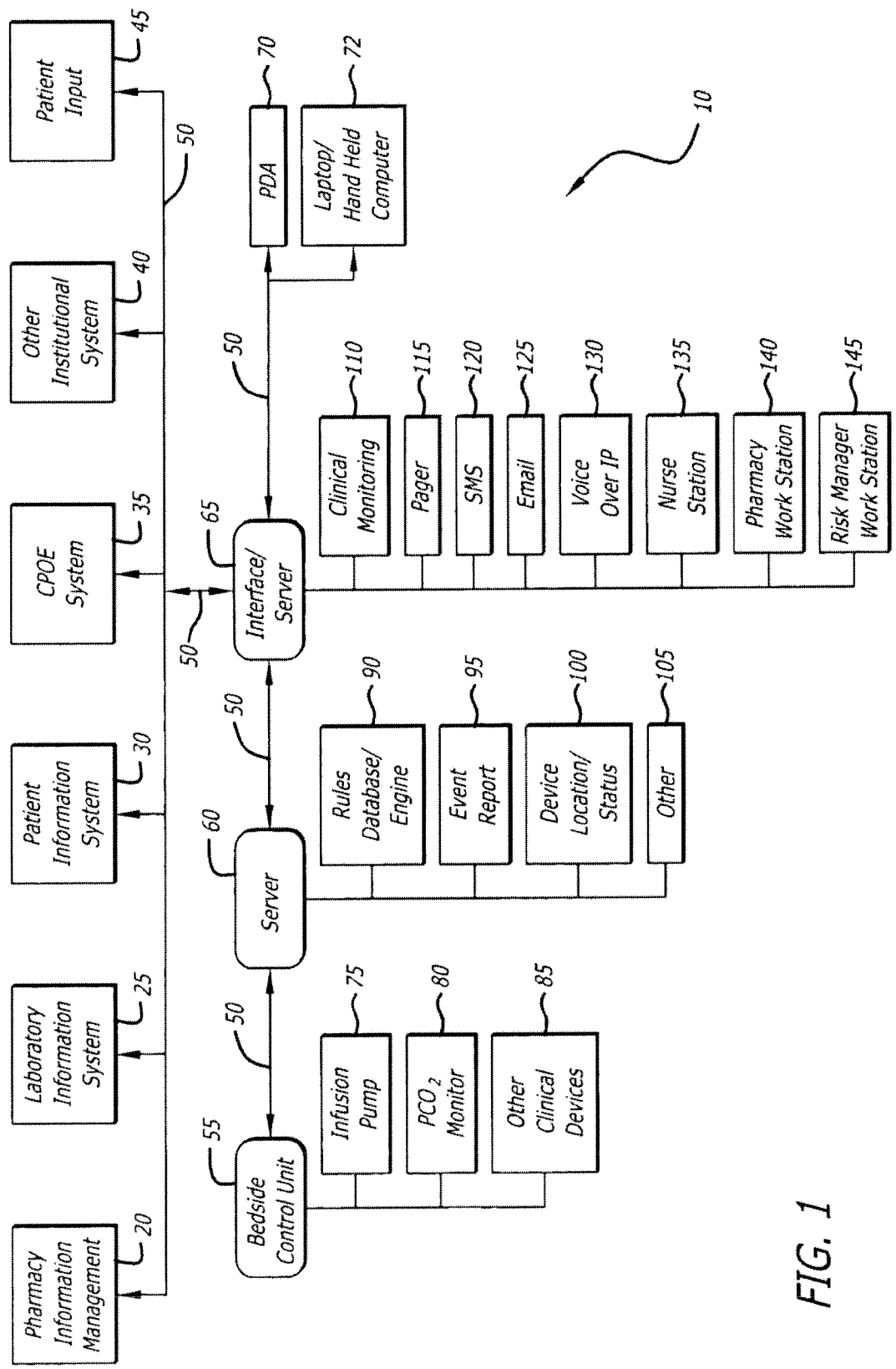
FIG. 1 is a schematic diagram of an institution-wide information and therapy management system incorporating principles of the present invention.

Referring now to drawings in which like reference numerals are used to refer to like or corresponding elements among the figures, there is generally shown in FIG. 1 an integrated hospital-wide information and therapy management system 10 in accordance with aspects of the present invention. The exemplary system depicted in FIG. 1 shows various institutional information systems, such as a pharmacy information management system 20, a laboratory information system 25, a patient information system 30, a computerized order entry system 35, a patient input system 45 and may include other institutional systems, such as other institutional system 40, as well. These systems are connected together using a suitable communications system 50, which includes various hardware, such as servers, routers, hard wire communication lines, and/or wireless network gear, such as wireless transmitters/receivers, routers, concentrators and the like. It will be immediately clear to those skilled in the art that such systems are programmable and function under the control and operation of suitable software programs that may be embedded in various hardware devices, stored as programs in server memory or otherwise available when needed and called for by the requirements of the systems.

The communications system 50 also connects the various institutional systems described above with various systems that administer and monitor delivery of medical therapy to patient's in the care giving institution. For example, there may be a bedside control or management unit 55 located in the general location of one or more patients, such as at a patient's bedside. The bedside controller 55 may be a dedicated device having a processor and memory and communication capability, and the processor is configured to run suitable software programs, that may be stored in controller memory or downloaded over communication system 50 that allow the controller 55 to receive and transmit information and device operating instructions or receive patient treatment parameters to program and operate a variety of clinical devices that are controlled by the controller 55. The controller 55 may also monitor the progress of treatment, including the start of treatment, and alarms or changes to the treatment plan occurring during treatment, and providing information about the course of treatment back to the system so that such information may be communicated to appropriate personnel or institutional systems. For example only, and not limited to, such devices as an infusion pump 75, $PCO_2$ monitors and other clinical devices such as a breathing rate sensor, pulse rate sensor, body temperature sensor, blood pressure sensor, urinary discharge volume sensor, an EKG sensor module, an EEG sensor module, an oxygen analyzer, a fetal monitor, a respirator, or other devices for maintaining blood sugar, providing electric nerve stimulation, providing physical therapy and the like may also be controlled and monitored by controller 55.

Bedside controller 55 communicates with other institutional systems using communication system 50. In one embodiment, controller 55 sends information to and receives information and/or operational commands or parameters from server 60. Server 60 includes various modules such as a rules database and engine 90, event reporting module 95, a module for tracking clinical device location and status 100, and other modules 105, such as a reporting module that may generate either standardized reports for use within the institution, or which may be programmed by input from care givers, technicians, or other institutional personnel to provide customized reports.

As depicted in FIG. 1, server 60 may be a standalone device, which may communicate over communication system 50 with other interfaces or servers, such as interface/server 65. Alternatively, interface/server 65 and server 60 may reside on the same physical device.

Interface/server 65 provides server services and interfaces for interfacing controller 55 and server 60 with other institutional information systems, such as the pharmacy information system 20, the laboratory information system 25, the patient (or hospital or clinical) information system 30, the computerized physician order entry system (CPOE) 35, the patient input system 45 and any other appropriate or available institutional systems 40. Additionally, interface/server 65 may include modules for monitoring clinical devices 110 connected to controller 55 or server 60, modules for sending alarms, alerts or other information to care giver personnel over a pager network 115, short message service (SMS) text messaging 120, email 125, voice over internet (VoIP) 130 and other modalities, such as a wireless personal digital assistant (PDA), wireless application protocol (WAP) enabled telephone and the like.

Interface/server 65 may provide status reports of administered therapy, allow input of information or modification of prescribed therapy regimes, and provide indications of alert or alarm conditions communicated by clinical devices in communication with controller 55 at nursing stations 135, a pharmacy work station 140, physician workstation and/or a risk management work station 145. Interface/server 65 may also communicate with remote equipment, such as a PDA 70, or a lap-top or hand held computer 72. Such mobile, remote equipment may be carried by care givers, or mounted on or otherwise associated with mobile institutional equipment to allow access by care givers to institutional data bases, allow for providing or altering therapy regimens, and for providing alerts, alarms or desired reports to care givers as they move about the institution.

Figure 2:
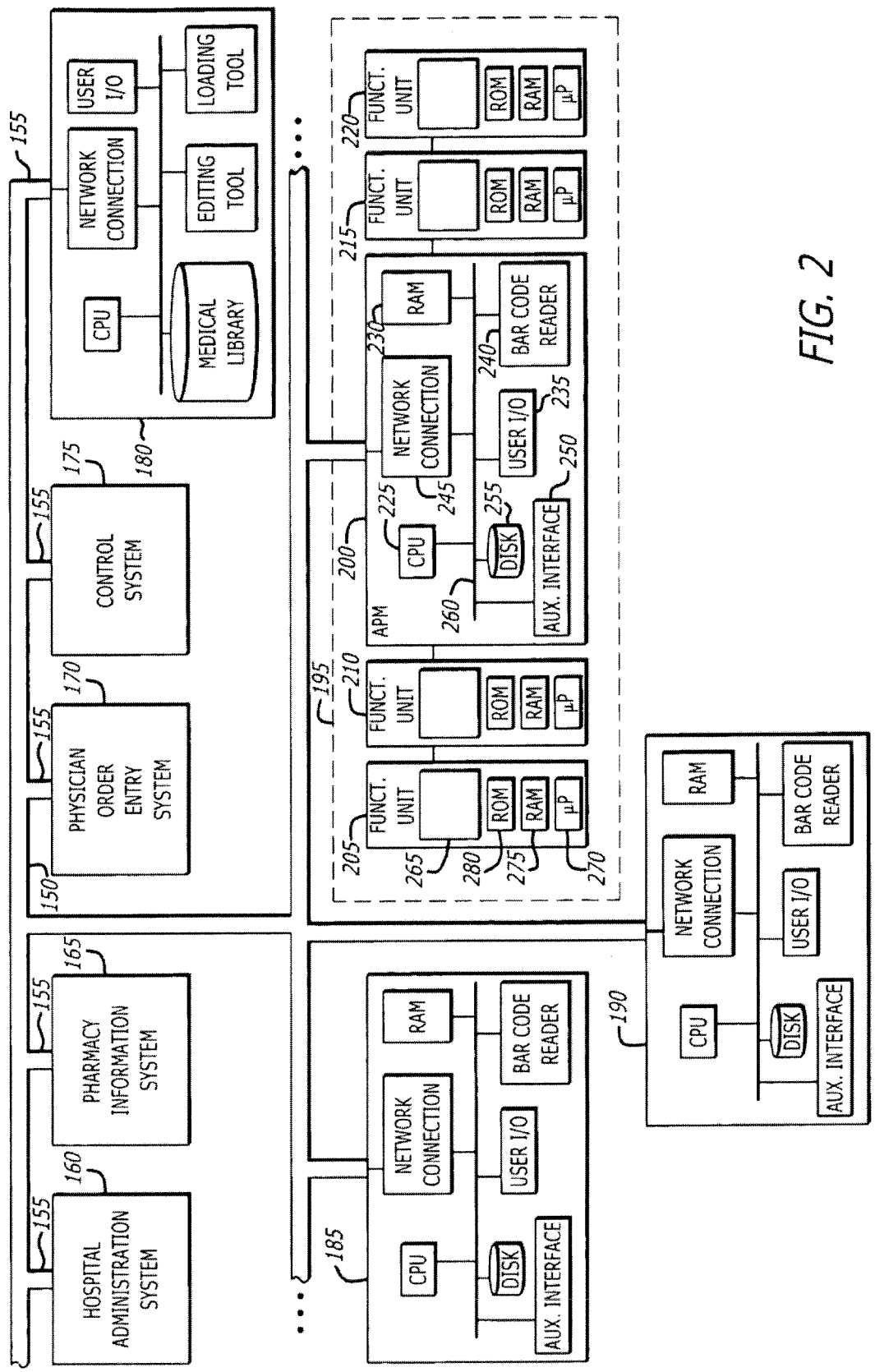
FIG. 2 is a schematic diagram showing details of elements of the institution-wide information and therapy management system of FIG. 1.

FIG. 2 depicts another example of a system incorporating aspects of the present invention and illustrating additional details of various components of the system. Various subsystems of the facility's information and therapy management system are connected together by way of a communication system 150. The communication system 150 may be, for example, a local area network (LAN), a wide area network (WAN), Inter- or intranet based, or some other communication network designed to carry signals allowing communications between the various information systems in the facility. For example, as shown in FIG. 2, the communication system 150 connects, through various interfaces 155, a hospital administration system 160, a pharmacy information system 165, a computerized physician order entry (CPOE) system 170, a control system 175, and a rules library 180. A plurality of patient care devices or systems 185, 190 and 195 may also be connected to communication system 150, either directly or through suitable routers, servers or other appropriate devices.

The communication system 150 may comprise, for example, an Ethernet (IEEE 522.3), a token ring network, or other suitable network topology, utilizing either wire or optical telecommunication cabling. In an alternative embodiment, the communication system 150 may comprise a wireless system, utilizing transmitters and receivers positioned throughout the care giving facility and/or attached to various subsystems, computers, patient care devices and other equipment used in the facility. In such a wireless system, the signals transmitted and received by the system could be radio frequency (RF), infrared (IR), or other means capable of carrying information in a wireless manner between devices having appropriate transmitters or receivers. It will be immediately understood by those skilled in the art that such a system may be identical to the system set forth in FIGS. 1 and 2, with the exception that no wires are required to connect the various aspects of the system.

Each of the various systems 160, 165, 170, 175 and 180 generally comprise a combination of hardware such as digital computers which may include one or more central processing units, high speed instruction and data storage, on-line mass storage of operating software and short term storage of data, off-line long-term storage of data, such as removable disk drive platters, CD ROMs, or magnetic tape, and a variety of communication ports for connecting to modems, local or wide area networks, such as the network 150, and printers for generating reports. Such systems may also include remote terminals including video displays and keyboards, touch screens, printers and interfaces to a variety of clinical devices. The processors or CPUs of the various systems are typically controlled by a computer program or programs for carrying out various aspects of the present invention, as will be discussed more fully below, and basic operational software, such as a Windows™ operating system, such as Windows NT™, or Windows 2000™, or Windows XP™, distributed by Microsoft, Inc., or another operating program distributed, for example, by Linux, Red Hat, or any other suitable operating system. The operational software will also include various auxiliary programs enabling communications with other hardware or networks, data input and output and report generation and printing, among other functions.

While the patient therapy and therapy management system of the present invention is described with reference to various embodiments encompassing institutional wide information systems, those skilled in the art will recognize that the concepts and methodology of the present invention apply equally to information systems having a smaller scope. Embodiments of the system of the present invention designed to provide the functions and features of the present invention at the ward or department level would include appropriate servers, databases, and communication means located within the ward to provide both wired and wireless connection between the various information systems, sensing devices and therapy delivery devices of the ward or department.

Modular Patient Care Device

Patient care devices and systems 185, 190 and 195 may comprise a variety of diverse medical devices including therapeutic instruments such as parenteral and enteral infusion pumps and respirators, physiological monitors such as heart rate, blood pressure, ECG, EEG, and pulse oximeters, and clinical laboratory biochemistry instruments such as blood, urine and tissue sample measurement instruments and systems.

In one embodiment, the patient care device 195 comprises a modular system similar to that described in U.S. Pat. No. 5,713,856 to Eggers et al., which is incorporated herein by reference. In this embodiment, the patient care device 195 comprises an advanced programming module or controller 200 (similar to controller 55 in FIG. 1), connected to one or more functional modules 205, 210, 215 and 220. Controller 200 includes a central processing unit (CPU) 225 connected to a memory, e.g. random access memory (RAM) 230, and one or more interface devices such as user interface device 235, a data input device 240, such as a key board or bar code reader, a network connection 245, and an auxiliary interface 250 for communicating with additional modules or devices. Controller 200 may also, although not necessarily, include a main non-volatile storage unit 255, preferably a hard disk drive, or alternatively, a read only memory (ROM), for storing software and data and one or more internal buses 260 for interconnecting the aforementioned elements. As shown in FIG. 2, patient care devices 185 and 190 may represent single-module patient care devices that include the same components as the controller 200.

In a typical embodiment, user interface device 235 is a touch screen for displaying information to a user and allowing a user to input information by touching defined areas of the screen. Alternatively, user interface device 235 could include any means for displaying and inputting information, such as a monitor, a printer, a keyboard, softkeys, a mouse, a track ball and/or a light pen. Data input device 240 is preferably a bar code reader capable of scanning and interpreting data printed in bar coded format. Alternatively, data input device 240 could be any device for entering data into a computer, such as devices for reading magnetic strips, PCMCIA smart cards, radio frequency cards, RFID tags, memory sticks, CDs, DVDs, or any other analog or digital storage media. Other examples of data input device 240 include a voice activation or recognition device or a portable personal digital assistant (PDA), lap top computer or other hand held computing device.

Depending upon the types of interface devices used, user interface device 235 and data input device 240 may be the same device. Alternatively, although data input device 240 is shown in FIG. 2 to be disposed within controller 200, one skilled in the art will recognize that data input device 240 may be integral within pharmacy information system 165 or located externally and communicating with pharmacy information system 165 through an RS-232 serial interface or any other appropriate communication means. Alternatively, data input device may be interfaced through any suitable institutional information system that is in communication, either directly, or through one or more servers, routers, concentrators or other equipment known to those skilled in the art. Auxiliary interface 250 is preferably an RS-232 communications interface, however any other means for communicating with a peripheral device such as a printer, patient monitor, infusion pump or other patient care device may be used without departing from the scope of the invention.

Digital Communication Methods

Network connection 245 is preferably a direct network connection such as a T1 connection, an integrated services digital network (ISDN) connection, a digital subscriber line (DSL) modem or a cable modem. Alternatively, any direct or indirect network connection may be used, including, but not limited to a telephone modem, an MIB system, an RS232 interface, an auxiliary interface, an optical link, an infrared link, a radio frequency link, a microwave link or a WLANS connection.

Modular Patient Care Devices

Functional modules 205, 210, 215 and 220 are any patient care devices under the control of the controller 200, for providing care to a patient or for monitoring a patient's condition. In one embodiment of the present invention, at least one of functional units 205, 210, 215 and 220 is an infusion pump module such as an intravenous infusion pump for delivering medication or other fluid to a patient. For the purposes of this discussion, functional unit 205 is considered to be an infusion pump module. Each of functional units 210, 215 and 220 may be any therapeutic or monitoring device including, but not limited to, an infusion pump module, a syringe infusion module, a Patient Controlled Analgesia (PCA) module, an epidural infusion module, a blood pressure monitor, a pulse oximeter, an EKG monitor, an EEG monitor, an end-tidal $CO_2$ ($etCO_2$) monitor, a heart rate monitor, an intracranial pressure (ICP) monitor, a glucose monitor or a temperature monitor. Alternatively, functional module 210, 215 or 220 may be a printer, scanner or any other peripheral input/output or communication device.

Each functional unit 205, 210, 215 and 220 communicates directly or indirectly with the controller 200, which provides overall control and display of the status of modular patient care device 195. In one embodiment, functional units 205, 210, 215 and 220 are connected physically and electronically in serial fashion to one or both ends of controller 200 as shown in FIG. 2 and as detailed in Eggers et al. However, one skilled in the art will recognize that there are other means for connecting functional modules with the interface unit which may be utilized without departing from the scope of the invention. It will also be appreciated that devices such as pumps or monitors that provide sufficient programmability and connectivity may communicate directly with the network without a separate interface unit. As described above, additional medical devices or peripheral devices may be connected to patient care system 195 through one or more auxiliary interfaces 250.

Each functional unit 205, 210, 215 and 220 typically includes module-specific components 265, a microprocessor 270', a volatile memory 275 and a nonvolatile memory 280 for storing information. It should be noted that while four functional modules are shown in FIG. 2, any number of devices may be connected directly or indirectly to the controller 200. The number and type of functional modules described herein are intended to be illustrative, and in no way limit the scope of the present invention. Module-specific components 265 include any components necessary for operation of a particular module, such as, for example, a pumping mechanism for infusion pump module 205.

While each functional unit is typically capable of a least some level of independent operation, controller 200 monitors and controls overall operation of modular patient care device 195. For example, as will be described in more detail below, the controller 200 provides programming instructions and power to the functional units 205, 210, 215 and 220 and monitors the status of each module receiving data for both display, coordination of control of other modules and for communication to connected medical devices and information systems.

Alternatively, the functions and features of a functional unit may be incorporated in a stand-alone unit. For example, while functional unit 205 is described as an infusion pump, it is contemplated that the same functions carried out by function unit 205 may be incorporated in and carried out by a stand-alone infusion pump. Such a stand-alone device may be in communication with the system through an appropriate communication device, such as a suitable communication port which may communicate with the communication system either by wired or wireless means.

Universal Configuration Database

According to one embodiment of the present invention, patient care devices and systems 205, 210, 215 and 220 are capable of being customized through installation of data, rules and operating parameters derived from a universal configuration database containing institutionally-established guidelines for medical treatments, such as a drug dosing parameters and rules, device operating characteristics and communication parameters. Each of the patient care devices or system 205, 210, 215 and 220 may comprise a different device type having at least some of its own distinct device operating characteristics or features.

Patient Identification

Assurance that the medication is being administered to the correct patient is also provided by this system. Upon entering the hospital every patient is typically issued an identification number (patient ID) and an associated wrist band. Printed on the band or located within the band is the patient ID in text form and in coded form. Various options exist for the coded ID. For example, the band could utilize a bar code, a magnetic strip, or any other means of storing coded patient identification information.

The wrist band or ID device may also include a wireless device that allows the ID device or band to be governed by an appropriate device at the patient location to passively, if not automatically, identify the patient. The patient's identity would then be provided, using either wired or wireless communication means, to whatever equipment at the patient's location required it. Similar technology may be used in conjunction with medication labels, discussed in detail below.

After a clinical device connected to the system of the present invention is powered up, the device displays on user interface 235 information pertaining to the current patient and/or the current location of the device. In one embodiment of the invention, this information is recalled from the last use of the device. Alternatively, the device location and or patient identification may be determined by information received through the communication system 150 within the institution. For example, referring to FIG. 2, a device 185, 190, 195 connected over communication system 150 to a server in a neonatal intensive care unit receives information from the server that it should be located by Bed 1, and that a particular patient is scheduled to be in that bed. Accordingly, the device 185, 190, 195 utilizes that information as the default patient and location. Alternatively, device 185, 190, 195 automatically determines its location within the hospital by a sensor or other means of uniquely determining its location. A sensor is defined broadly herein as any device or process of sensing or detecting the location of a device, including, but not limited to, a network receptacle or port address, a network adapter, programmed location instructions, hospital records indicating location, an IR sensors or tags, RF sensors or tags, magnetic sensors or tags, or any other means of detecting the location of a device 185, 190, 195.

After determining its location, the device queries the user whether the patient information entered into the memory of the device is correct. If the patient is new to the device, or if the information is missing or incorrect, the user enters the patient ID into the device using user interface 235. Patient ID is typically entered using an input device, such as bar code reader 240, by scanning a patient's coded wristband including patient identification information. Alternatively, patient ID may be entered manually using a keyboard, keypad, or other input device, including devices that utilize wireless technology and sensors, such as, for example, RFID tags. The clinical device determines if the current configuration database it is using to operate and deliver therapy to the patient is correct for the needs of the particular patient by querying various institutional information and rules databases that the processor of the clinical device may access over communication system 150. If the current configuration dataset is missing or incorrect, the user is prompted to select the appropriate configuration dataset such as, for example, by selecting a configuration dataset according to clinical location, patient, physician, and the like. Alternatively, the appropriate configuration dataset ID may scanned into the system from the patient's identification band, or may be automatically retrieved from memory or from another location in communication system 150 once the patient identity, location or other patient-specific information is entered into device or system 185, 190, 195.

Order Entry/Verification

When a physician orders an IV, or therapy regimen to be administered to a patient, the order is typically first sent to the pharmacy where it is entered into the hospital's pharmacy information system. The order may either be written on a simple prescription slip or entered directly into the CPOE system 35 (FIG. 1). Most hospitals include a pharmacy computer system capable of maintaining records of medications already given as well as those prescribed in the future. The pharmacy information system typically provides a library of drug allergies and adverse drug interactions against which each incoming prescription is checked for as part of the prescription entering/drug dispensing process to identify possible allergies and adverse drug interactions and help in preventing administration of drugs to a patient where the patient might be injured by the prescribed course of therapy. Additionally, the system may check to determine if any therapies are being duplicated, such as where two or more drugs might be used to treat a diagnosed disease, whether they are synergistic or antagonistic, and whether the prescribed therapy should be modified accordingly.

In some institutions, there is no centralized pharmacy. Instead, drugs are prepared in the ward or department, and sometimes at the bedside, by skilled care givers. In these instances, the order is sent to a care giver authorized to receive and/or prepare the order. The ward or department is equipped with a system such as that described above, except that its operation may be localized to the ward or department. This system is capable of providing all of the information to the care giver as the institution wide system. Moreover, both the pharmacy system, and ward or department based systems, when operating in accordance with the principles of the present invention, may also be embodied in systems that also provide advice for the administration of specific medications, such as, for example, recommendations to give the drug at a specific time, such as within thirty minutes of a meal, directions to keep the drug cold, or warm, and the like, directions to infuse the drug only through an opaque infusion set to prevent degradation of the drug due to light exposure, and the like. The system may also modify the recommendations provided in view of changes in the status of the patient that are noted and entered into the system, either manually or automatically.

Moreover, the system according to the present invention may also provide for the planning and administration of a sequence of drugs or other therapies, including alerting the care giver if the timing of the planned sequence falls out of sync, such as when a planned delivery of a drug or therapy is overdue, or was given early. The system may provide not only alerts, but also other reports to provide care givers needing such information with a view into the status of the medications and therapies planned or being delivered to patients. Various embodiments of the system will typically allow the records of the planned or already administered drugs or therapies to be sorted in a variety of ways, such as, for example, by drug name, as needed or requested by a care giver.

After the order is entered the medication to be administered to a patient is prepared, typically in the pharmacy, but in some cases, in a ward, at a nurse station, or at a location where local inventories of drugs are stored. The pharmacy information system 20 typically prints a label for placement on the medication with text characters or other encoded information identifying the medication, the patient for which it is intended, and other information, such as operating parameters for communication to an appropriate clinical device to program the device to deliver the medication in accordance with the original prescription order.

For example, where the medication is to be delivered using an infusion pump, the medication label preferably includes at least the following information: patient name, patient ID, patient location, infusion protocol reference, infusion protocol deviations, or deltas, if any, and scheduled time of infusion. Additionally, for a continuous infusion, the label may include the drug name, dose, diluent (if any), drug concentration and infusion rate. Similarly, for an infusion that is to be given intermittently or as needed, the label may include the drug name, dose, diluent, concentration and administration schedule. The label is affixed to the medication container before the prescription is transported to the unit nursing station. Medications are preferably transported from the pharmacy to the nurse's station by institutional personnel, pneumatic tubes or contained within drug dispensing cabinets near the nurse's station. Alternatively, drugs may be transported using a robotic system, such as a PYXIS system (Pyxis Corporation, San Diego, Calif.). If the drug is to be distributed from a unit nursing station, then the same type of label may be printed, or hand written, at the nursing station and affixed to the drug container.

At an appropriate time, the labeled medication container is then taken to the patient's location. The bar code reader, or other data input device, including passive devices designed to automatically query devices associated with the various ID and medication labels, is used to scan the coded drug label, the patient's coded ID band and the caregiver's ID badge, and any supplementary prescription information or medical device configuration instructions, including configuration dataset ID, contained on the label, an accompanying order, or otherwise made available for entry or downloading into the medical device or system once confirmation of the patient and medication is completed, such as by reading information from a memory media or code contained on or within the label. The scanned information is stored in the memory of the device, such as, for example, in RAM 230 (FIG. 2), while device or system 185, 190, 195 first compares the scanned data to ensure that the patient identity corresponds to the patient information on the medication label, and that the prescription is being administered at the appropriate time.

After the correct patient, prescription and time are verified, device or system 185, 190, 195 may be programmed using either manual entry of various operating parameters, parameters retrieved from the medication label (or medication transaction carrier). Alternatively the device may be programmed by retrieving appropriate functions and commands from the active configuration database, the protocol or other program information identified on the container label. Default parameter values may be adjusted by any delta information included in the prescription. The user is prompted to enter, using a touch pad, bar code reader, or any other appropriate means, any missing or incomplete data. Optionally, some data may be obtained automatically via communication system 150 or from the appropriate department server based upon the entered patient ID, caregiver ID, user commands, etc.

Once all required settings have been entered, 185, 190, 195 displays the values, either serially or in one or more groups, to the user for verification. The configuration dataset is also accessed to check the entered infusion parameters according to the protocols, rule sets or other guidelines for that configuration. If any incorrect or out of range entries are detected, an alert may be activated to inform the operator. In no case will a medication be allowed to be delivered to a patient unless the patient ID from the patient's wristband and patient ID from the medication label match. In one embodiment, clinical operating parameters are only communicated to the clinical device when a comparison of the ID scanned from a patient matches the patient ID scanned from the medication label. In another embodiment, where the medication label includes clinical operating parameters that may be scanned and communicated to the clinical device to program the clinical device to deliver the medication in accordance with the prescription order, the processor of the device will only allow the clinical operating parameters to be scanned from the label if the scanned patient ID and the patient ID on the medication label match.

As will be discussed below, this verification process may include other steps to ensure that the right medication is being delivered to the right patient at the right time and in the right manner. For example, the processor of the clinical device may compare the timing of the delivery to a log of previous medication deliveries to determine if it is appropriate to deliver the medication at this time, or if the interval between a previous administration is shorter than set forth in a database of institutionally determined rules and best practices. Alternatively, such a comparison could also determine if the interval is too long, indicating that a drug administration has been missed or is late, requiring reporting and/or adjustment of one or more delivery parameters for the current medication delivery. The system may also be programmed to provide an alert to care givers notifying the care givers that the timing of the drug administration is not as scheduled and requires investigation/evaluation and/or adjustment.

Once all information is entered and verified, the clinical device is ready for operation, and the delivery of the medication to the patient may be started automatically, or by a command from the user. Where the clinical device comprises a central controller 200 and one or more functional devices 205, 210, 215, 220 (FIG. 2), controller 200 communicates with the appropriate functional module or modules to program the functional module(s) to perform the prescribed treatment.

It should be noted that the prescription label or other treatment instructions (such as are communicated over the communications network 150 once verification has been accomplished) may identify multiple drug delivery schedules and other instructions. The multiple drug delivery schedules (or a single complex drug delivery schedule) may define a plurality of operations to be performed by clinical device 195. For example, the prescription label or prescription order could identify a multichannel coordinated infusion drug delivery schedule involving multiple channels and infusion solutions. Additionally, the same order may identify a delivery schedule for (or detail instructions for) programming a functional module, stand-alone infusion device or auxiliary device to monitor the patient physiological parameters, such as a blood pressure, heart rate, $O_2$ saturation, respiratory rate, and the like. Controller 200 monitors the measured parameters and, depending upon active rule sets and other configuration instructions, can modify infusion parameters based upon signals received from the physiological monitors. Such feedback systems may be useful for titration of drugs, to control anesthesia, or to regulate blood pressure.

In one embodiment of the invention, bedside controller 55 (FIG. 1) may be used by a nurse, physician or technician to access institutional databases to display a variety of information about a particular patient. This information can include an on-line, real-time, graphical patient electronic medication administration record (eMAR) that is derived from the patient's medication profile maintained by the institutions pharmacy information system 30. The controller 55 also allows remote access to a patient's records stored on institutional systems to display, for example, medication history, laboratory results, and stored treatment regimens for the patient. For example, the medication history includes a listing of all drug or other treatments including past, present and future deliveries to the patient. Additionally, access to records of the institution's administration systems 20, 25, 30, 35, and 40 is available through the network 50. Alternatively, this information may also be stored, as will be discussed in more detail below, in a medication database carrier, the pharmacy information system, or a separate system dedicated to collecting, analyzing and producing reports concerning various alerts or clinical "events" that are recorded or logged during the administration of medical treatment to a patient.

In another embodiment of the present invention, a database including a library or libraries of information concerning past and present medical administration activities and/or institutional guidelines for appropriate parameters for administration of various medications may be stored on server 60. For example, the guidelines may include institutionally established guidelines or limits on drug administration parameters, such as dosage, frequency of administration, and other delivery related information such as, for example, appropriate flow rates and infusion durations for programming infusion pumps. Additionally, the guidelines may encompass guidelines for providing drug administration appropriate to particular patient treatment areas having different sets of delivery parameters for similar medications, such as medication administration directed to geriatric, pediatric and oncology patients. Guidelines may also be included that are directed to particular therapy regimens, such as chemotherapy regimens or regimens for treating chronic infection or pain. It will be understood that such a database could also be stored on a server or system associated with a particular institutional system, such as, for example, a module associated with the pharmacy information system 20.

As described previously, each bedside controller 55 can be connected through an appropriate interface to a variety of peripheral equipment. For example, referring to FIG. 2, controller 200 may include a barcode reader 240 capable of reading barcodes on a patient's wristband or medication container; an infusion pump 205 for delivering medication to the patient in a predetermined, controlled manner; or various other functional units 210, 215, 220 that can automatically monitor a patient's vital signs and send signals representative of these vital signs to the controller 200. Controller 200 may either store this information for later retrieval, or communicate this information through network 150 for storage and analysis by a selected software application to provide a graphic display of the patient's vital signs during the course of treatment. Additionally, the information for the patient may also be correlated with information associated with the treatment of the patient, such as laboratory results or other patient information to allow for the generation of reports concerning the progress of the patient's treatment, and also to assist care givers in determining the best course of treatment for the patient. Such information may also be filtered through rules database/engine 90 (FIG. 1) to provide intelligent alerts or alarms to care givers, or to suggest changes to the treatment of the patient.

The therapy management system's application software that is responsible for managing the operation of the embodiments of the present invention and for interfacing with other institutional systems is typically modular in construction to allow installation and operation of the system with only one or more of the application software groups present. This provides flexibility in meeting the widely varying needs of individual institutions where cost and complexity may be an issue or where the full system is not needed. Each of the modular applications, however, is fully integratible into the system.

The programs of the therapy management system control alarms or alerts generated by one of the modular applications. Alarms are routed automatically to the appropriate video display. For example, an occlusion alarm generated by a pump 75 (FIG. 1) may remain local for a predetermined period. After that period the controller 55, or servers 60, 65 may broadcast the alarm by causing the alarm to be communicated over the network 50 to alert other hospital staff of a potential problem or to cause a particular person responsible for the care of a patient, such as, for example, a physician or nurse, to be paged, provided with text message or email, or other method of communication. A severity level of the alerts or alarms may be determined by the institution. The severity level of the alerts may also be escalated as determined by the institution, depending on the response or lack of response to the alert by care givers in the institution.

The operation of various modular applications that can be incorporated into the system of the present invention will be discussed more fully below. In one embodiment, the system includes a medical administration management module which integrates medical order information, infusion pump monitoring, and barcode technology to support the real-time verification and charting of medications being administered to a patient. The medical administration management module creates and maintains an on-line, real-time, patient-specific electronic medication administration record ("eMAR") or integrated medication administration record ("IMAR") for each patient.

This medication administration module contains all of the information generated in the institution regarding the care provided to the patient. The medication administration management module gathers information from the various bedside controllers that are distributed throughout the institution. For example, when a physician attending a patient diagnoses an illness and determines an appropriate course of treatment for the patient, the physician may prepare a handwritten medical order specifying the desired therapeutic treatment as well as any appropriate parameters such as dosage and/or period of administration. The written prescription is sent through the institutional mail system to the pharmacy where it is then entered into the pharmacy information system 20 through a dedicated terminal, or other means, and is then entered into the therapy management system.

In another embodiment, the physician accesses the pharmacy management system 20 or the CPOE system 35 through a dedicated terminal or through the therapy management system via the network 50 using a remote information entry device, which could be a nursing CPU, a bedside controller 55 (FIG. 1), or some other device, such as a hand held or lap top computer, or PDA. Alternatively, the treatment order may be entered by a nurse or other qualified caregiver into either the pharmacy management system 20 or the CPOE system 35.

Bar Code

Referring now to FIGS. 3-5, a variety of implementations of the barcode identification system of the present invention are shown. FIG. 3, for example, shows a patient identification bracelet 300 of the kind typically used in hospitals and other institutional settings to ensure that each patient is able to be identified even if the patient is unconscious or otherwise unable to respond to questioning. A barcode 305 is printed on a label that is attached to the patient identification bracelet 300 and has encoded within its sequence of bars the information necessary to identify the patient. This barcode may be read using a computerized barcode reader 240 such as that shown connected to the controller 200 (FIG. 2). Generally, the barcode reader 240 comprises a light emitting and receiving wand that is scanned across the barcode. The light emitted by the wand is reflected by the sequence of dark and light lines comprising the barcode into the receiving lens of the wand. A sensor in the wand converts the received light into a signal that is then transmitted to the controller 200. A software application program running on the controller 200 then decodes the signal into the data represented by the barcode in a manner well known to one skilled in the art. Using appropriate software programs, this data may then be automatically entered into a database stored in the controller's 200 memory 230 or disk storage 255. While a barcode has been described for purposes of illustration, those skilled in the art will immediately understand that other systems, such as magnetic stripes, or programmed punched holes may also be used to represent data stored on each label, care giver badge or patient wrist band. Alternatively, a bar code reader may be incorporated into the housing of controller 200 such that the bar code to be read need only be passed over the reader, or alternatively, placed in a position adjacent to the reader so that the reader can read the bar code.

Barcode systems are extremely flexible and the amount of information that can be represented by the barcode, while limited, can be used in a variety of ways. For example, as depicted in FIG. 4, a drug container 310 is identified by a label 315 having a barcode 320 printed thereon. This barcode 320 can represent the patient identification and the medical order number, and any other information the institution finds helpful in dispensing the drug and tracking the treatment. The barcode 320 may also be read using a barcode reader, and, using suitable application software such as that included within the medical administration management module, discussed below, can be used to link the drug container and its contents with the patient identification bracelet 300 affixed to a patient to ensure the right drug is delivered to the right patient at the right time in the right manner.

The use of barcodes is not limited to the implementations discussed above. For example, a sheet 325 of barcode labels 330 having barcodes 335 is shown in FIG. 5. Such labels can be produced by a printer connected to the pharmacy information management system 20 or CPOE system 35 (FIG. 1) of the therapy management system of the present invention, or, alternatively, by any other printer connected to any other hospital information system that can be programmed to produce barcodes bearing the information in a form that can be read by the barcode readers connected to the various controllers or computers of the therapy management system. These barcode labels 330 may then be affixed to clinical devices, patient belongings, or other items where positive identification is needed.

Alternatively, other devices may be affixed to the patient, drug, nurse or medical device that may communicate with the therapy management system using wireless means. For example, IR or RF transceivers may be incorporated into medication database carriers or other identification devices that are capable of interfacing and communicating with the therapy management system. Other wireless technologies may also be used.

Figure 6:
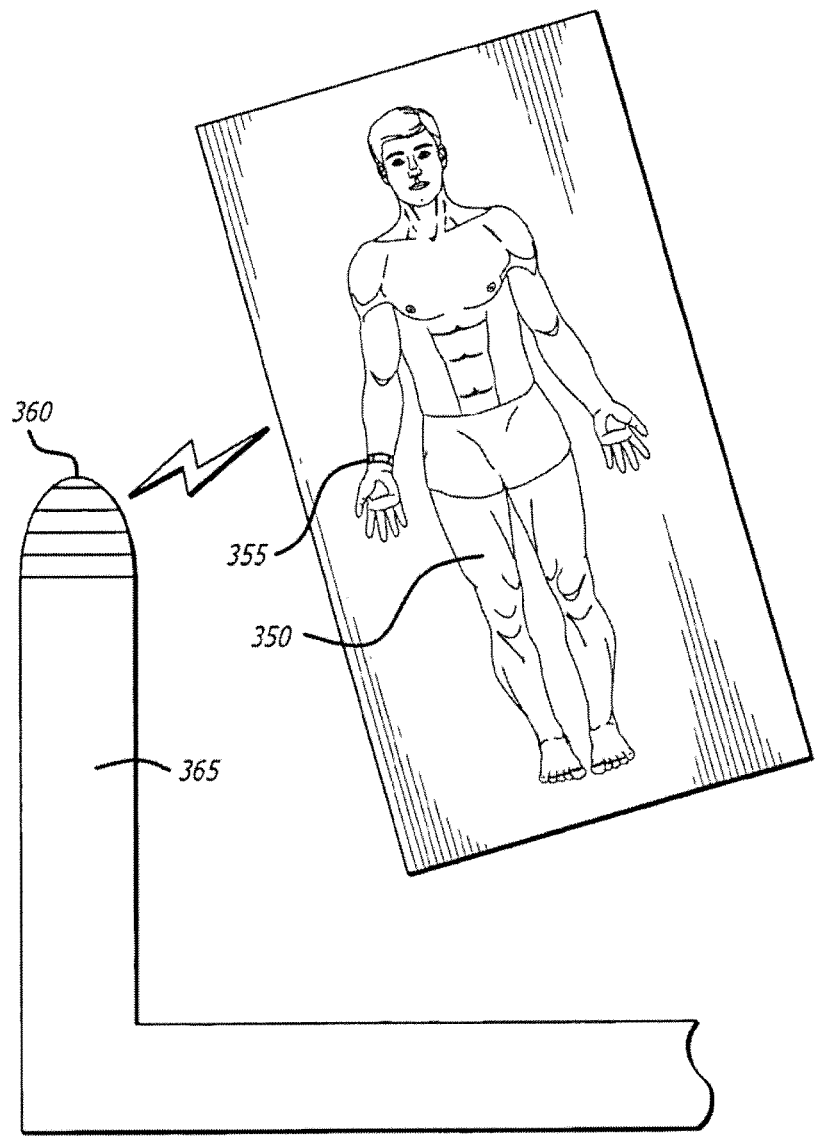
FIG. 6 presents a view of a patient having an identification device located on his arm that interacts with a transmitter/receiver located adjacent the patient's bedside.

Another embodiment of the therapy management system is shown in FIG. 6 wherein the patient 350 and/or caregiver have badges or wrist bands 355 that may also include electronic circuitry that is responsive to signals from a transmitter/receiver 360 located in each patient room or treatment area to automatically provide the therapy management system with the identity of, and possibly other selected information about, the occupants of the patient room or treatment area, eliminating the need to use a bar-code reader to read the bar-codes on the patient and/or caregiver badges or wrist bands. Such a system may be described as a passive recognition system in that neither the patient nor the caregiver need take any active steps to inform the therapy management system of their location within the institution.

One example of such a system incorporates an intelligent RF computer chip into the caregiver or patient badge or wristband 355 that provides a unique, or programmed response to a RF transponder or reader 360 located within a patient room or treatment area, such as in the frame 365 of the entry or exit of the room or treatment area, or mounted on a wall or ceiling. Each badge or wrist band 355 interacts with signals of the transponder 360 in a unique way, the unique interaction representing an assigned code for the badge or wristband 355. Utilizing this technology would remove manual steps and some of the "human factor" from the process of identifying the patient and caregiver.

When an individual 350 wearing a badge or wristband 355 having such a circuit enters a room or area where a transmitter/receiver 360 is located, the electronic circuit in the badge or wristband 355 interacts with signals emitted by the transmitter without any positive action on the part of the caregiver or the patient. This interaction may be sensed by the receiver, which may be capable of determining the identity of the badge or wristband 355 from the interaction of the electronic circuit with the emitted signals. Alternatively, the receiver may simply sense the interaction and provide a signal representative of the sensed interaction to a computer or other processor which has been programmed or otherwise configured to determine the identity of the individual associated with that particular badge or wristband 355.

Although the preceding paragraphs describe a passive recognition system using electrical circuitry, other approaches may also be used. For example, it can be envisioned that the patient and/or caregiver may have magnetically-encoded devices that can be automatically read by an appropriate detector located in the patient room or treatment area.

Where an embodiment of the therapy management system incorporating the present invention maintains an on-line, real-time, patient specific graphical medication administration record that includes both past, present and future scheduled medications, a nurse may select a scheduled dosage on the eMAR and indicate that it will not be administered for specified reasons selected from a list of options that are dependent upon the health status of the patient at a particular time. This system also allows a nurse to select a scheduled dose on the eMAR, and record notes and observations about the dose selected from a list of options. The system of the present invention also provides on-line, real-time help screens that can be accessed by a nurse or other caregiver to display specific information about selected medication and dose to be dispensed. These screens may be displayed at the nurse station, on the user interface 235 of controller 200 (FIG. 2), a PDA, lap top or hand held computer, or any other suitable display device capable of receiving information communicated by the system.

In another embodiment, the therapy management system of the present invention provides a list of on-going infusions that can be displayed on the video display of the pharmacy information management system 20, 165 in the pharmacy. Drug administrations that will terminate within a preselected time period may be distinguished from other administrations by color highlighting or other means. The time remaining, drug, and patient name may be presented as well as buttons for program control.

In another embodiment, the therapy management system of the present invention records and maintains in a stored file a log of alerts and other therapy related information that are generated when any discrepancy is identified, for example, during the verification process which will be discussed more fully below. The system provides programming that also allows the care giver to acknowledge and correct the discrepancy in real-time, or override the alert by entering the appropriate command. Even where the care giver is allowed to override the alert, the therapy management system prompts the care giver for a reason for each alert override and then automatically enters the reason into the eMAR for the patient.

The therapy management system may also track specific alert conditions that are reported by specific medication administration or monitoring devices indicating that particular treatment parameters have not been correctly entered into the device by a caregiver or that certain monitored parameters are out of an acceptable range, as determined by comparing the treatment or monitored parameters to a database of acceptable limits, rules and good practices determined by the institution. These alerts, or "events" may be either automatically stored in a database associated with the therapy management systems, such as in a storage media associated with servers 60 or 65, or associated with some other institutional information system. Alternatively, the alerts may be stored in a dedicated event logging/analysis and reporting server. The analysis may generate reports for a specified medication administration device or the analysis may consolidate event reports from all, or a selected subset of the medication administration devices in an institution, and may provide reports in accordance with either customized formats or formats pre-established by the institution.

In another embodiment of the present invention, a clinical monitoring and event history module designed to monitor a variety of clinical devices attached to the network in a real-time manner and provide information about those devices to monitoring stations located elsewhere on the network may be included as one of the programs running on servers 60, 65, or as part of other institutional systems 40 (FIG. 1). For example, the clinical monitoring and event history module can be configured to monitor a plurality of clinical devices that are in use to deliver medication to patients in the private rooms, semi-private rooms or ward areas in a nursing unit. The clinical monitoring and event history module retrieves real-time data from each device, and displays a visual representation of each device including all significant data related to its status and settings on video displays located at the bedside, nursing station, pharmacy, or other locations within the institution as needed, including on displays associated with remote devices, such as, for example, hand held or lap top computers, PDA's or other portable, remote devices in communication with the therapy management system.

For example, in the case where the clinical monitoring and event history module is monitoring an infusion pump, a nurse at the nursing station can access the status for that pump wherein the display attached to the nurse computer located at the nursing station then displays information regarding the status of the infusion being performed at that time. For example, information can include the name of the drug being infused, the patient's name, the scheduled start, the actual start of infusion, the scheduled end of infusion, the projected end of infusion, the amount of drug infused, the amount of drug remaining to be infused and any alert or discrepancy conditions that may need attention by the nurse. Additionally, other patient specific information, such as information received from various monitoring devices connected to the system, or lab reports or other information, such as allergy information retrieved from a patient's profile stored in the institution's patient information system 30, may also be available and displayed to the care giver.

Because the therapy management system of the present invention is a fully integrated system, all of the components of the therapy management system work in concert so that a nurse, doctor or technician may, after evaluating the status of the infusion displayed on either the video display at the nursing station or on the user interface 235 of controller 200 (FIG. 2) at the bedside may, by using an appropriate input device, such as, for example, a keyboard, the touch screen, or other input device of the computer, adjust the infusion regimen accordingly using, for example, a screen displayed on the video display.

Intelligent Alarms

The clinical monitoring event history module may also be programmed to immediately display alarm conditions on remote monitoring screens, such as the video display attached to the nursing station, as the alarm occurs, or it may send electronic messages to a care giver's pager, or text messaging enabled cell phone or other such device. The alarm may also be sent via email, or via voice over IP through the internet. For example, the status of each patient's infusion can be represented on a video display at the nursing station. When an alert occurs, the box representing the patient's room flashes red to attract attention to the alert. Displaying the alarm condition in this manner allows a nurse to quickly and easily identify the patient from the nursing station and take appropriate action to address the condition causing the alarm. The system may also be programmed to display certain alarms that have been identified as particularly important events at other video displays located throughout the institution, such as the video display attached to the pharmacy information system located in the institution's pharmacy.

Because many alarms are generated by conditions that will not result in immediate harm to a patient, such as when a respiration monitoring device detects that a patient is breathing at a rate slower than is normal, but whose blood oxygenation level is within normal bounds, one embodiment of the present invention includes a system for analyzing alarms and categorizing them into a hierarchy of importance. The system does this by applying rules and guidelines established by the institution to the alarm state to determine if the priority or importance of the alarm is such that immediate notification of care givers is necessary, or if the alarm state can be allowed to remain for a period of time until it can be evaluated and corrected.

The alarm analysis module may also be programmed to track the occurrence of alarms and the time before the alarm state is corrected. For example, if a period of time elapses since an alarm state was detected that is longer than a predetermined period of time, the priority of the alarm may be escalated, resulting in the alarm being communicated to care givers.

In another embodiment of the present invention, the various modules of the therapy management system tracks the administration of therapy to a patient, including the results of various laboratory tests performed on the patient or the patient's blood. This data may also be integrated with information received from various clinical devices that are monitoring the patient's vital signs, such as blood pressure, $EtCO_2$ or $SpO_2$. Applying rules and guidelines stored in a database of information reflecting acceptable levels and good practices of the institution, the programs of the therapy management system of the present invention may analyze the data and identify when a prescribed therapy is achieving a desired result, and may also identify when the desired results are not being achieved, indicating that adjustments to the therapy being delivered to the patient require adjustment. In another embodiment, the therapy management system may analyze the various patient related data from the laboratory system, vital signs monitoring devices and therapy administration devices and by applying rules and guidelines stored in a rules database to the analyzed information and suggest alternative courses of treatment, or adjustment of current treatment parameters, to achieve a desired result.

In another embodiment, the therapy management system of the present invention includes a clinical device tracking and reporting module used to maintain a record of the location of each clinical device and the history of its use in the institution. This system maintains a record of the current or last known location within the institution of each clinical device used in the institution, such as an infusion pump or vital sign sensor. Thus, the appropriate equipment can be easily located by a nurse or a technician for a given therapy regimen or vital sign measurement. This is particularly useful in a large hospital or clinic having many patient rooms, patient beds, or treatment areas where equipment may be temporarily misplaced. This system is also useful in those particular instances where an emergency occurs where treatment requires a particular piece of equipment. The status of that equipment can be easily ascertained from a video display, such as that available at a nursing station, or may be displayed on the display of a portable or remote device, such as a PDA or other suitable device.

The clinical device tracking and reporting module also maintains a record containing the usage history of each clinical device, including information about the patient it was used to treat, its location, the date, time, duration of use, any alarms that occurred and what medications were dispensed. This history may also contain the maintenance and calibration records for a clinical device. Such information can be queried on-line by technicians, nurses or other hospital administration personnel to generate reports to assist in locating the clinical device, report on the historical usage of the device, and to provide a log of preventative maintenance and equipment calibration. The efficient calibration of complex and sensitive clinical devices is particularly important in a heath care institution to maintain accuracy and quality of therapeutic treatment delivery. Maintaining a history of the usage of the device is also helpful to justify purchasing additional clinical devices when needed, or where the record indicates that a particular clinical device has become obsolete and needs to be replaced by a newer model of the device.

In one embodiment, the therapy management system of the present invention includes a knowledge resource tools module that provides a framework for information sharing among the various units in the hospital and also supports an assortment of everyday tools to use by the nurses, physicians and technicians involved in the delivery of health care within the institution. This module allows or assists in integrating external information sources into the care system to improve the effectiveness of the care management team in treating the patients in the institution.

For example, the knowledge resource tools module may provide a variety of on-line tools including, for example, a calculator, a dose rate calculator for calculating the appropriate dosage and infusion rate for a particular drug to be infused into a patient, a standard measurement conversion calculator for converting between units of measurement, a body surface area calculator, and a timer and stopwatch. These resources may be displayed on the video displays at appropriate points within the system, and are available from any computer, either local, portable or remote, located in the pharmacy, at the nursing station or at the bedside. These application tools can be programmed to appear on the video displays either automatically, such as, for example, when an infusion pump is configured at the start of an infusion to assist in the calculation of a dose rate. These resources may also be available upon entry of the appropriate command by a nurse, physician or technician.

One embodiment of the therapy management system of the present invention may include an event logging/analysis and reporting module. This module may be implemented in a variety of ways. For example, the event logging system may be part of an institution's medication administration management module, it may be a separate module, or it may be implemented in a different computer system, which may or may not be located in the institution. For example, in one embodiment, event logging/analysis and reporting module may be resident on a third party computer system located outside of the institution, but in communication with the institution's systems using a wired or wireless, or combination of both, communication system.

A common feature of the various configurations of the event logging/analysis and reporting module is that the module receives, or retrieves, information from medication administration devices generated by the medication administration device before or during administration of medical treatments to a patient, analyzes the information, and then provides reports related to the received or retrieved information to the institution. These reports may be used by the institution to improve the delivery of medication to patients in the institution, by identifying frequently occurring errors or conditions that can be corrected through improvements to the medication delivery process or training of caregivers. Such reports may either be customized on demand, that is a caregiver or other individual responsible for analyzing the events may request a custom report, or the system may provide a menu of reporting formats pre-established by the institution that may be selected by the individual or department requesting the report. Alternatively, the system may be automated so that reports in pre-established formats are produced and distributed to appropriate individuals or departments in the institution at preselected intervals. Such a system will typically be embodied in one or more databases stored in a memory from which therapy related information may be extracted and analyzed using a processor controlled by an appropriate software program. The results of the analysis may be stored in a memory for future use or distribution, or may be printed using a printer.

As depicted in FIG. 1, the therapy management system is connected to other systems in the institution via a network 50. This network may support standard health level 7 (HL7) interfaces to the hospital's other information systems and can also support custom interfaces to systems or devices that do not support the HL7 standard. The system interfaces may be either real-time or batch mode, although a real-time interface to an institution's pharmacy system may be required to support the on-line medical administration records keeping.

The therapy management system software can be written to operate on a variety of operating systems to suit the needs of a variety of institutions. In a present embodiment, the software is written to interface with the nurses and physicians using the Windows environment (Windows is a trademark of Microsoft, Inc.) on IBM compatible micro-computers. The Windows environment is well-known by those skilled in the art and will not be described in detail herein. The therapy management system software, when implemented using the Windows system, is particularly useful in that the Windows operating system provides the ability to load several programs at once. Multitasking programs, allowing several application programs to run simultaneously yet providing immediate access to the various software modules of the therapy management system may also be used.

Y-Site Compatibility Checking

Figure 7:
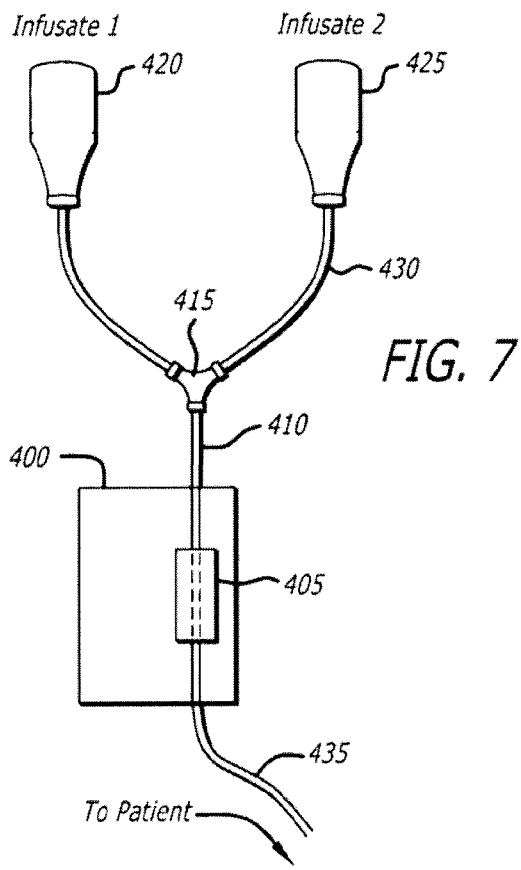
FIG. 7 is a graphical representation of an infusion set up showing primary and secondary infusion fluid sources providing primary and secondary infusion fluids through a Y-site connector for infusion into a patient.

There are often times during the course of an infusion therapy regimen when a second drug is prescribed for infusion at the same time a first drug is being infused into a patient. In many instances, this secondary infusion is accomplished by using a "Y-Site" connector that provides access to the primary infusion source line. Such an infusion set up is depicted in FIG. 7, which shows an infusion pump 400 having a peristaltic pump 405 with a source line 410 installed therein. Source line 410 includes a Y-site connector 415. Those skilled in the art will appreciate that the concepts of the invention are equally applicable to any other kind of pump. A primary infusion fluid source 420 provides infusate to be delivered to the patient through a line, the Y-site connector 415 and source line 410 to pump 405 for infusion through output line 435 to a patient. The Y-site connector also provides an additional connection through which a second infusate contained in infusion fluid source 425 may flow through a secondary source line 430, through Y-site connector 415 and source line 410 into pump 405. This type of set up may be used in several different modes, for example, to provide for sequential delivery of infusion fluids to a patient, or for simultaneous delivery of two different fluids to a patient. In still another variation, secondary source 425 may be omitted, and the secondary infusate delivered to source line 410 by injecting the second infusate through a port in the Y-site connector 415 using a syringe.

An embodiment of the present invention is directed to solving a problem that often arises when a multiple source infusion regimen is to be carried out. In some cases, the first and second (or third, or other infusate) may not be compatible with each other, requiring, for example, that mixing of the drugs be prevented, or that infusion of the second drug be delayed for a period of time. Even if the care giver is aware of the potential problems caused by such an infusion, there is typically no way to check for such incompatibilities and alert the care giver.

In this embodiment of the therapy management system of the present invention, the bedside controller 200 (FIG. 2) has stored in its memory what drug is being infused in the primary line. When the care giver identifies the second medication to be delivered to the controller, either by using the bar code reader (240) or some other means, such as, for example, and as described previously, by reading an RFID tag attached to the drug, or by receiving information through communication system 150 from some other institutional information system. In one embodiment, the information from some other institutional system is triggered by when the medication is detected by a wired or wireless transmitter/receiver present in the patient's room or otherwise associated by the patient that informs the controller 200 of the identification of the drug.

Figure 8:
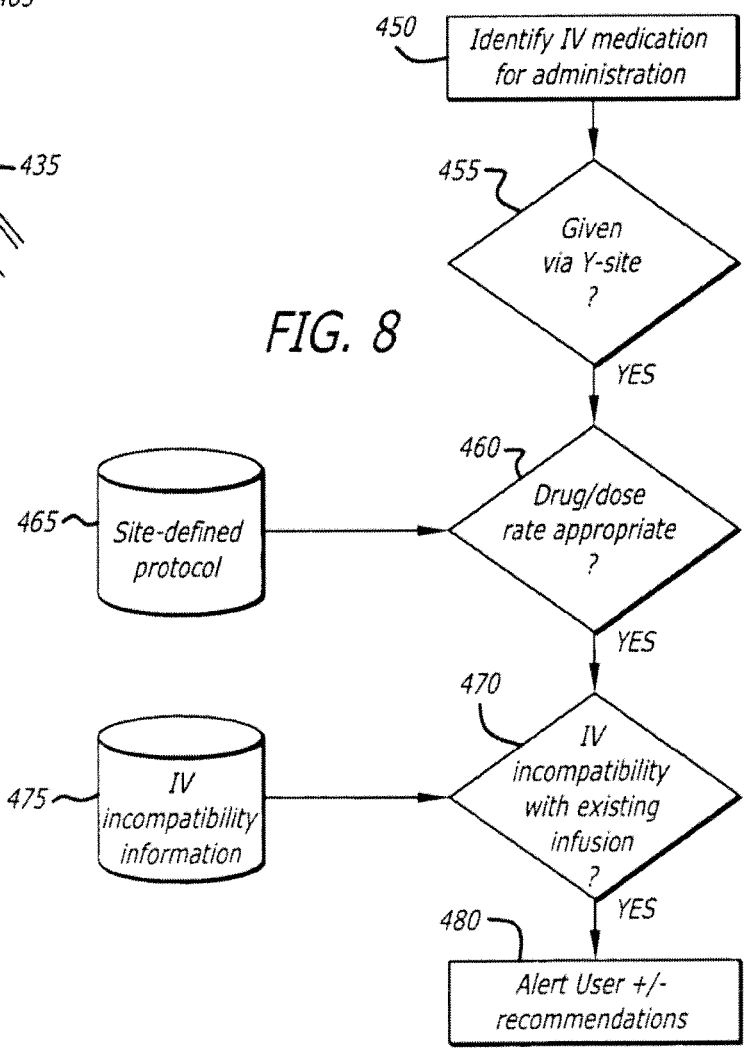
FIG. 8 is a flow chart illustrating one embodiment of the system of the present invention carried out by programming commands embodied in software running on the controllers, servers and information systems of the present invention that determines whether drugs intended to be infused through a Y-site connector are compatible.

The flow chart depicted in FIG. 8 illustrates the logic carried out by one embodiment of the present invention that checks the databases present on the institutional system to determine if the second drug may be safely delivered to the patient. As set forth above, the identification of the medication to be delivered to the patient is entered into the system in box 450. The system displays a prompt on user interface 235 inquiring whether the drug is to be delivered using a Y-site in box 455. If the answer to this query is no, the system carries on with other processes as deemed appropriate for the particular drug. If the answer to the prompt in box 455 is yes, the care-giver enters the dose rate and other pertinent parameters into the system, and the system determines whether those delivery parameters are appropriate for the patient to which the drug is to be delivered in box 460. This determination is carried out by comparing the entered parameters with site-defined rules and protocols stored in database 465, which may be stored in the memory of the controller 200, or may be available somewhere else on the system, such as server 60 (FIG. 1) and which may be accessed by controller 200 through communication system 150.

If the system determines the operating parameters are inappropriate for the patient, the care giver is alerted, and may either change one or more of the parameters until the system indicates the operating parameters are appropriate, or may override the alert and direct the system to proceed. A record is typically stored in the memory of the controller 200 of all alerts and over rides for later analysis and reporting.

If the operating parameters are determined to be appropriate in box 460, the system determines whether the drug to be dispensed is compatible with existing infusions in box 470 by comparing the present infusion and second drug to a database 475 of drug incompatibility information. As before, database 475 may be stored in the memory of the controller 200, or it may reside on a server accessible to the controller 200 through communication system 150. If the drug is not determined to be incompatible with present or previous infusions, then the care giver completes the setup of the controller and initiates the infusion. However, if the drug is determined to be incompatible in box 470, the care giver is alerted to the incompatibility in box 480. The alert may also include recommendations for correcting the problem, such as, for example, recommending a different drug to be delivered, or a waiting period before beginning the infusion. These recommendations may be site-defined or provided from a database of standardized recommendations.

Pharmacokinetic Modeling

Figure 9:
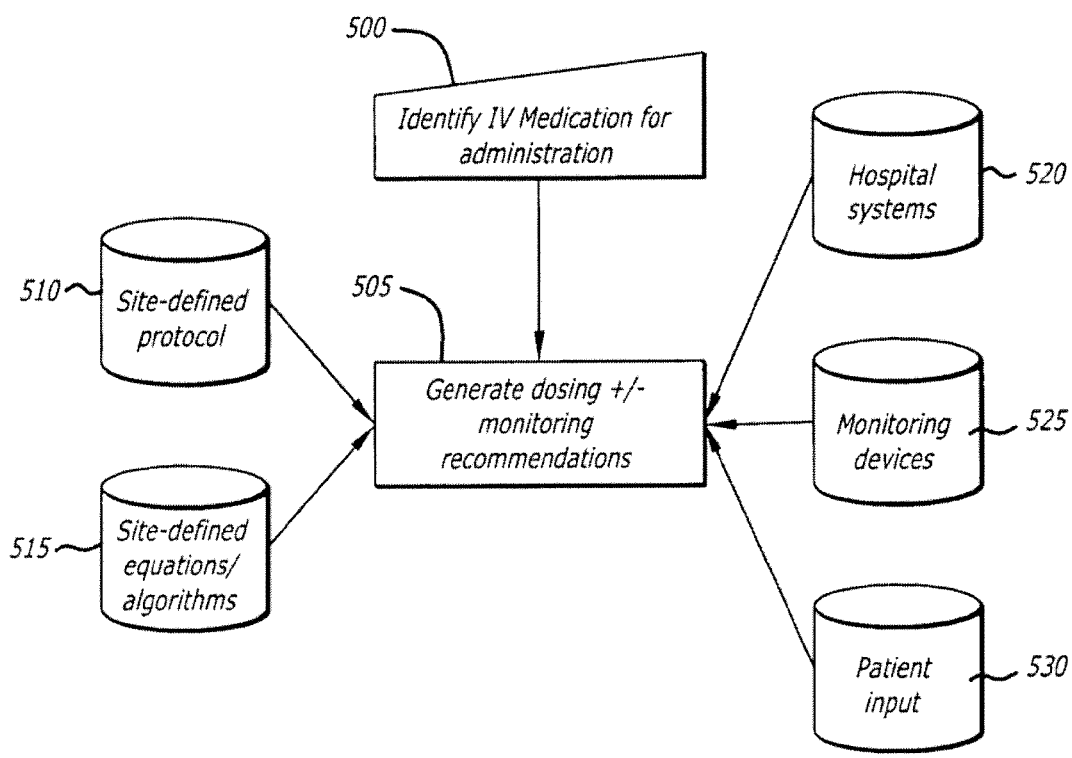
FIG. 9 is a flow chart illustrating one embodiment of the system of the present invention carried out by programming commands embodied in software running on the controllers, servers and information systems of the present invention that generates dosing and monitoring recommendations.

FIG. 9 depicts another embodiment of the therapy management systems of the present invention that combines patient specific information with site-defined rules incorporating pharmacokinetic equations and algorithms to assist care givers by generating a proposed dose, and/or monitoring schedule, based on target therapeutic ranges for a condition being treated.

Pharmacokinetic (PK) models permit computation of the theoretical time distribution and concentration (disposition) of an infused drug within various compartments of the body including blood plasma and various "effect site" tissues. Inputs to the PK model typically include the time course of dose (Q), the drug's "parameters" obtained from controlled clinical studies and patient characteristics such as weight, age, gender, blood volume, renal clearance if available.

For example, a simple PK model estimates the concentration of drug in the blood plasma (Cp) as a function of the duration of a constant continuous drug flow Q as follows:

$$Cp(t) = Q/(K*Vd)*(1-e(0.693*t/t\frac{1}{2}))$$

where the parameters are:

t is time elapsed
Q is the drug flow
t½ is the half-life of the drug
Vd is the volume of distribution Many drugs have a narrow range of optimum concentration (C) above which they exhibit toxicity and below which there is no effect. Optimal delivery of medication therapy considers the general PK characteristics of each drug as well as patient-specific factors such as age, blood volume and renal clearance which may modify these characteristics.

One embodiment of the therapy management system of the present invention employs pharmacokinetic models defined by the institution to provide both initial guidance and continuing feedback to the care giver related to the delivery of medication to a patient. In a typical application, a drug is selected for delivery within a given profile for a specific patient. Pertinent patient-specific data is retrieved by the system and used to optimize the PK model for this patient. Alternatively, the system may request that the care giver enter appropriate patient information into the system to facilitate calculations using a selected PK model. There may be more than one PK model, including a plurality of PK models associated with specific drugs. Thus, in some instances, the care giver will select the appropriate PK model to use by making a selection from among a list of PK models presented to the care giver by the system.

Using the selected PK model, the embodiment of the therapy management system of the present invention may provide recommendations concerning bolus and continuous dose rates needed to achieve the desired level of the drug within the patient's plasma. The therapy management system is programmed to monitor the levels of the drug within the patient's plasma or blood and provide the clinical device delivering the drug, typically an infusion pump, with dynamically updated dose limits for bolus and continuous dosing. Further, in one embodiment of the system of the present invention, the system provides ongoing computation of compartment concentrations which are compared with institutional defined compartment limits to provide alerts, alarms and other guidance directly through the infusion system as well as via secondary communication methods such as pagers, cell phones or other hospital information systems.

For example, sodium nitroprusside may be administered to a patient experiencing acute hypertension to lower the patient's blood pressure. Sodium nitroprusside, a potent vasodilator, is typically infused by IV with an initial bolus dose followed by a continuous maintenance dose intended to rapidly achieve a specific target effect-site concentration.

When the patient is admitted to the institution, the patient's age, weight, gender and other specific data are entered into the institution's information system and thus may be accessed and retrieved by the therapy management system of the present invention. The patient's blood pressure may be continuously monitored using, for example, a monitoring device designed to monitor blood pressure in the patient's radial artery. Samples of the patient's blood, urine and other fluids or tissues may be drawn to evaluate the patient's hematology and renal function. All of this information may be stored in one or more databases resident on the institutions information system or systems, and are accessed and retrieved as needed by the therapy management system of the present invention. The therapy management system applies a selected PK model to evaluate the patient's data and, based upon the evaluation, make specific recommendations regarding bolus and continuous dosing amounts which are within the institution's defined limits for the delivery of nitroprusside.

Later, when appropriate laboratory testing results, such as results for renal function, for the patient are entered into the system and become available, the system evaluates this data to determine the appropriateness of the initial limits used to determine the recommended delivery parameters. For example, if the laboratory test results indicate that renal clearance is limited, the upper dosing limit for delivery of the nitroprusside to the specific patient may need to be readjusted. Additionally, the effect-site concentration limit may be lowered as a function of the sub-optimal renal clearance to avoid buildup of toxic metabolic by products of the nitroprusside. If renal clearance is exceptionally poor, the system may recommend use of alternate medication for regulation of blood pressure.

Pharmacodynamic (PD) measurements and models describe the relationship between drug concentration at its effect-site (compartment) and a physiological response such as blood pressure, heart rate, level of consciousness and the like. While drug pharmacokinetics provides a means to estimate the current and future drug disposition (concentration and/or amount) in various compartments based on the time course of drug infused, the physiological response is typically measured by instrumentation and/or clinician evaluation. These physiological responses are entered into the institution's information system or systems and may be accessed and retrieved the another embodiment of the present invention to assist care givers in the delivery of care to a patient. For example, institutionally determined dosing and effect-site limits may be automatically modified by the therapy management system as a function of present and past PD evaluations as well as other patient specific factors.

Referring again to the example of sodium nitroprusside infusion, a suitably programmed embodiment of the present invention may access and retrieve stored data representing sequential measurements of arterial blood pressure for a specific patient and compute the effect-site drug concentration. The system is programmed to evaluate this data and calculate a pharmacodynamic concentration-response curve for the patient. From this response curve, the patient's sensitivity to changes in effect-site concentration may be determined from the rate of change of the response to the effect site concentration. The patient's response sensitivity, in turn, may be used by the system to generate recommendations related to adjusting the dosing therapy to achieve a specific clinical target such as a reduced blood pressure level. For example, an estimate of the relation between blood pressure and effect site concentration of nitroprusside by the system would inform the care giver of how much to increase or decrease dosage in order to achieve the desired endpoint. Further, in another embodiment, the system may provide the care giver with specific recommendations for modifying the dosing protocol to achieve the desired effect.

Some drugs, such as the anesthetic propofol, given as a primary sedation agent, and remifentanil given as a primary analgesic agent, exhibit synergistic interactions. When given simultaneously, the effect on sedation is much greater than for either drug given separately. Such interactions may be monitored by the various embodiments of the system of the present invention. The system may apply rules determined by the institution to represent the best practice within the institution for delivering such a combination of drugs to ensure that the delivery parameters prescribed by the care giver are appropriate. If the system determines the parameters are not appropriate, the system may alert the care giver, and, in some embodiments, provide the care giver with recommendations for adjusting the delivery parameters of the drugs to ensure that delivery of the drugs is performed as set forth by the institutionally determined rules. Moreover, the system, applying the PD model in accordance with clinical and laboratory results, as well as pertinent patient information, may dynamically adjust the defined dose and compartment concentration limits. Alternatively, the system may make recommendations for such adjustments to the care giver. For example, where propofol and remifentanil are to be administered to the patient, lower dosage limits and compartment limits for both medications would be indicated, and this information would be provided to the care giver for the care giver's consideration, or, in some embodiments of the present invention, the limits would be automatically adjusted by the system as appropriate in view of the institutions established guidelines and the patients physiology and condition.

The use of PK and PD models, along with application of institutionally determined rules, when applied to planning and adjusting the therapy delivered to a patient can be thought of as an automated system similar to that used to control the flight path of an airplane. A course of therapy is planned for a patient based upon patient information, such as physiology and condition, disease diagnosis and generally accepted best practices within an institution. As the therapy progresses, the patient's condition, as represented by the value provided by various monitoring devices, laboratory results and patient input (such as a patient's scaling of his or her pain, for example) are monitored by the system. Where there are results that indicate a problem, either current or potential, the course, or flight path, of the therapy may be adjusted by the system to provide for the best outcome for the patient. These adjustments may take the form of adjustments to dosing parameters, recommendations for adjustments or changes to the therapy, or notifications or alerts to the care giver that the therapy or some aspect of the therapy needs attention. Thus, the present invention includes closed-loop control of the therapy to the patient based upon the information available to the system, including the planned course of therapy and the on-going outcome of that therapy as determined from the devices monitoring the patient and the results of laboratory or other tests carried out on the patient.

As in previously described embodiments, a medication or drug to be administered is identified to the therapy management system by inputting the information on, for example, the label of the medication into the system using, for example, a bar code reader, in box 500 of FIG. 9. Running appropriately designed software, the system generates a recommended dosing and monitoring schedule in box 505. The recommended dosing and monitoring schedule is developed using information stored in a database of site-defined treatment protocols 510, a database of site-defined equations and algorithms 515, information from other hospital or institutional systems 520, information received from monitoring devices 525, which may be received directly from the monitoring devices, or retrieved from information generated by the monitoring devices, such as blood pressure, temperature, laboratory results and the like, and stored in a database accessible to the system using the communication network. Finally, patient input may also be used as a factor in generating a recommended dosing and monitoring schedule. For example, information about the patient's age, weight, gender, allergies and other conditions and the like may be used by the system to develop an appropriate dosing and monitoring schedule. Additionally, information from the patient regarding the patient's assessment of his or her condition, such as a patient's rating of pain he or she is experiencing, may also be inputted into the system.

Once an infusion has been initiated, various embodiments of the therapy management system of the present invention embodied in suitable software programs operating on one or more servers of the system, or on a controller such as controller 200 (FIG. 2), or both, monitor the infusion and the collection of information about the condition and status of the patient from various monitoring devices and laboratory instruments or information systems. Additional embodiments of the present invention include programs embodied in suitable software that use the information received from the therapy administration devices and clinical monitoring devices to assist the care giver in modifying the treatment regimen delivered to a patient to improve the patient's course towards a desired outcome.

For example, modifying the operating parameters of an infusion pump after the start of an infusion may trigger the application of various rules, pharmacokinetic equations, and/or other institutional guidelines to the proposed parameter changes. Should the proposed changes be determined by the system to be inappropriate for one or more reasons, the system will provide an alert or alarm to the care giver, nurse station and/or pharmacy, or care giver. In some instances, the alarm or alert may be over ridden; in other cases, further operation of the infusion pump may be blocked by the system until the parameter value is changed to an acceptable value.

In another embodiment, the system monitors information related to a particular patient that is generated by various clinical monitoring devices or by institutional laboratory tests. In this embodiment the system, applying protocols and guidelines established by the institution, monitors the patient's data to determine if appropriate testing has been performed and that the results of the testing or monitoring are within institutional guidelines. If, for example, the system does not detect that a required test has been performed within an intuitionally determined period, the system sends an alert to caregivers, nurse stations, pharmacy stations or any other suitable workstation of information viewer in communication with the system. The priority of the alert or alarm may be dynamically adjusted based upon the condition being monitored, the patient's past medical history, condition or other characteristics, the timeframe since the last data was received, and whether a caregiver has taken any action in response to a previous alert or alarm.

Figure 10:
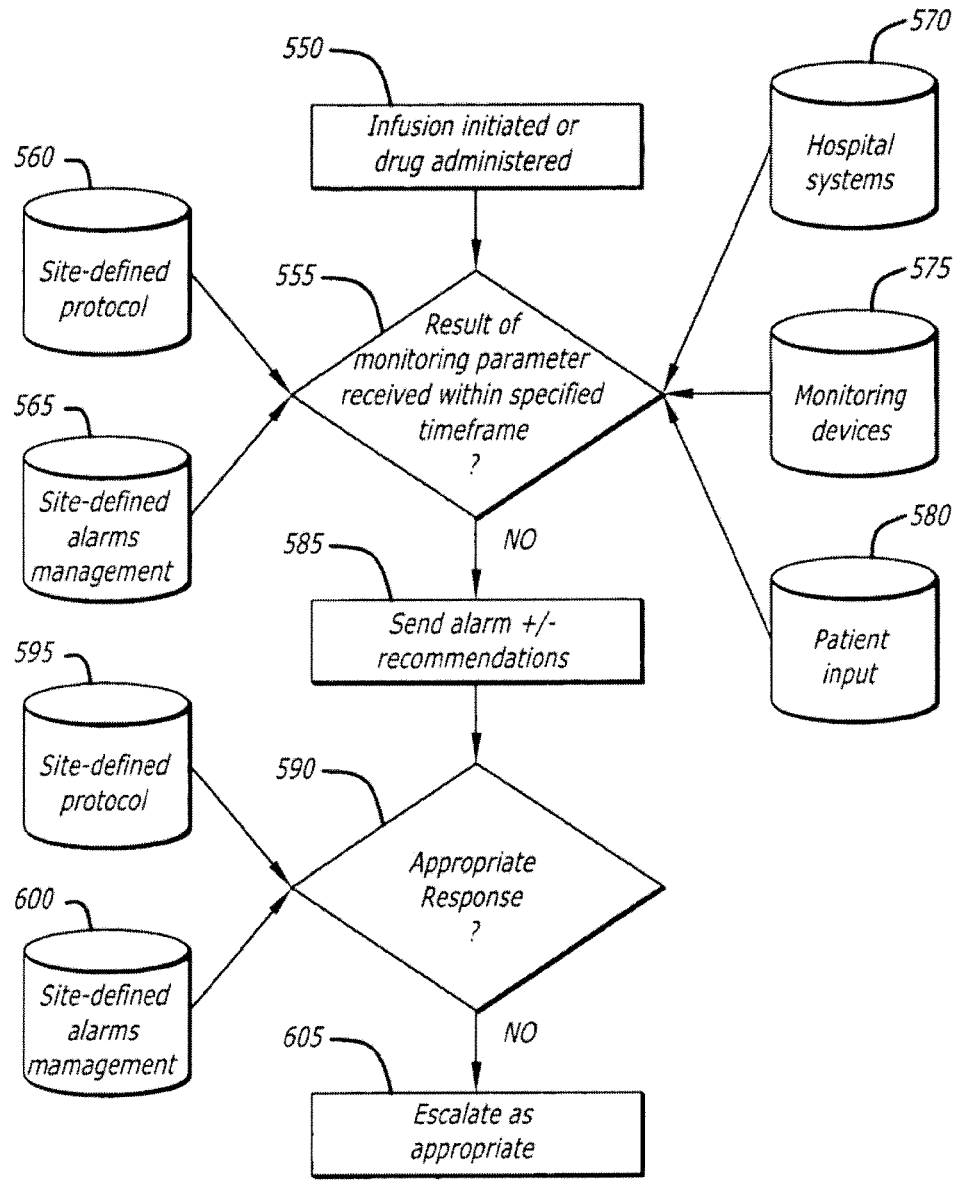
FIG. 10 is a flow chart illustrating one embodiment of the system of the present invention carried out by programming commands embodied in software running on the controllers, servers and information systems of the present invention that monitors information flowing through the system to determine if the results of a test or monitoring parameter are received within a specific timeframe and provides an appropriate alert if necessary.

An example of a process embodying aspects of the present invention is set forth in the block diagram of FIG. 10. After an infusion has been initiated or a drug administered in box 550, the system monitors the various information databases accessible to it through the communication network systems, such as that shown in FIGS. 1 and 2. If the particular patient or drug profile associated with a given therapy calls for monitoring of one or more aspects of the patient's condition at specified timeframes, or at a specific time of day, the system checks to see if the results of such monitoring are stored in the various information databases within the specified timeframe in box 555. In determining whether a result has been received in a specified timeframe, the system accesses and retrieves information from other institutional systems, such as a database of site-defined protocols 560, a database of site-defined alarms management rules 565, other hospital information systems 570, monitoring devices 575 and patient input 580.

If the determination in box 555 is that a required result has not been received in the specified timeframe, the system sends an alert, which may also be accompanied by one or more recommendations for correcting the condition that caused the alert, to one or more specified persons or work stations in box 585. The system then continues to monitor the information flowing through the institution's systems to determine if an appropriate response to the alert or alarm is entered into the system in box 590. This determination is based on comparing the response received with the information in a database of site-defined protocols and rules 595, and with the information stored in a database of site-defined alarms management rules and guidelines 600. Databases 595 and 560 may be the same database or different databases. Similarly, databases 600 and 565 may be same or different databases. If the system, in box 590, determines that an appropriate response has not be received, the system may then escalate the priority or severity of the alert or alarm in box 605 as deemed appropriate, again with reference to institutionally determined protocols, rules and guidelines.

Figure 11:
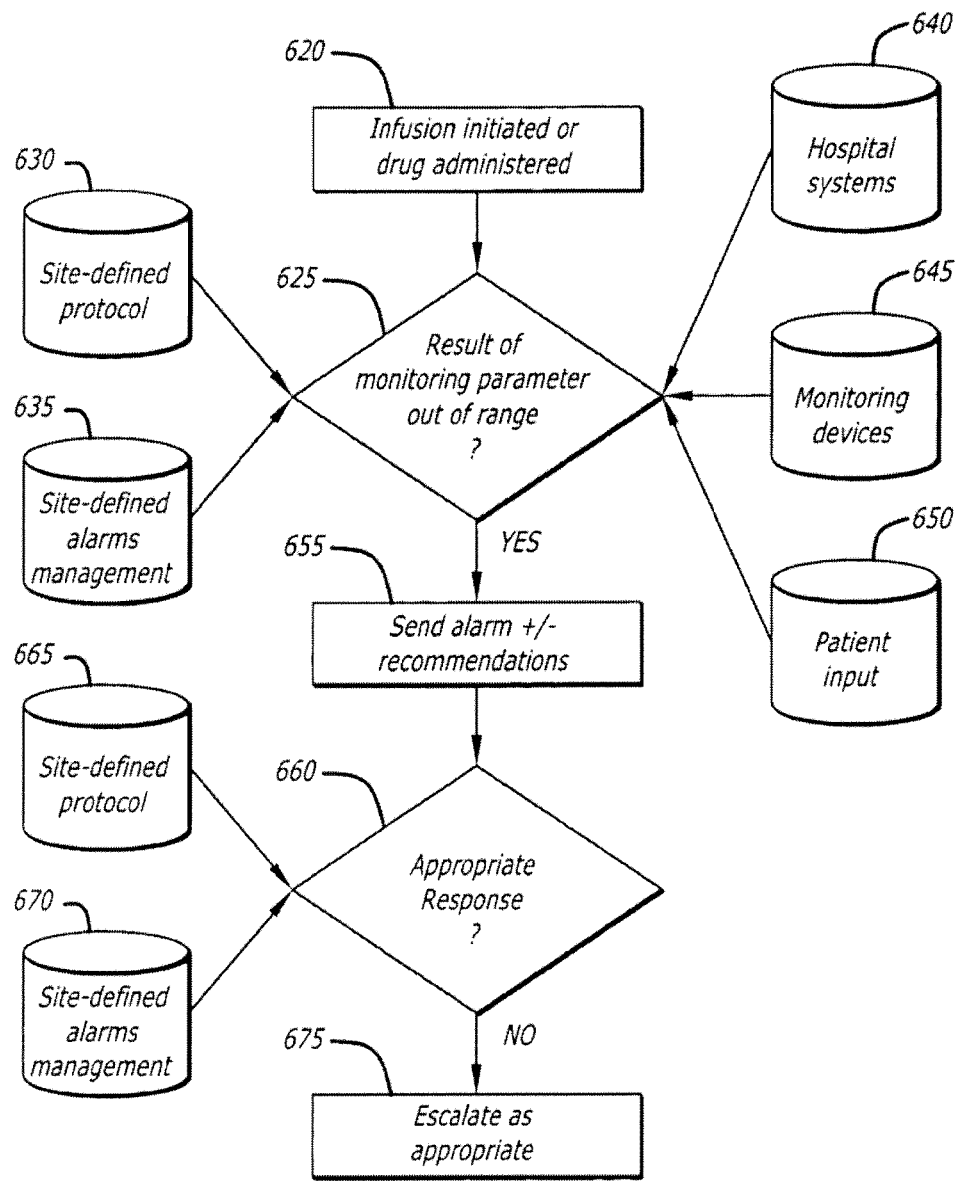
FIG. 11 is a flow chart illustrating one embodiment of the system of the present invention carried out by programming commands embodied in software running on the controllers, servers and information systems of the present invention that determines if the result of a parameter being monitored by the system is within a specified range and provides an appropriate alert where the result is out of range.

Similarly, when monitoring results are received by the system, whether within a specified timeframe or otherwise, the system analyzes the received monitoring result or parameter to determine if the value of the result or parameter is within a range of expected values of that parameter, given the therapy regimen being administered and the patient's profile and condition. An example of an embodiment of the present invention incorporating aspects of such a system is depicted in the flow chart of FIG. 11.

After the infusion is initiated or a drug administered in box 620, the system monitors the various institutional information systems and clinical devices in which it is in communication for the entry of results of tests, such as laboratory tests, or values communicated by clinical devices monitoring the condition of the patient. Once these results are entered and detected by the system, the system analyzes the result to determine if the result is within orange of acceptable values in box 625. This determination utilizes information stored in a database 630 of site-defined protocols, rules, or pharmacokinetic and/or pharmacodynamic equations, a database of site-defined alarms management rules or guidelines 635, information available from other institutional systems 640, monitoring devices 645 and input from the patient 650.

If the system determines that the result is out of range in box 625, the system sends an alert or alarm, which may also be accompanied by one or more recommendations for correcting the condition that caused the alarm, to one or more specified persons or work stations in box 655. The system then continues to monitor the information flowing through the institution's systems to determine if an appropriate response to the alert or alarm is entered into the system in box 660. This determination is based on comparing the response received with the information in a database of site-defined protocols and rules 665, and with the information stored in a database of site-defined alarms management rules and guidelines 670. Databases 665 and 630 may be the same database or different databases. Similarly, databases 670 and 635 may be same or different databases. If the system, in box 660, determines that an appropriate response has not be received, the system may then escalate the priority or severity of the alert or alarm in box 675 as deemed appropriate, again with reference to institutionally determined protocols, rules and guidelines.

Figure 12:
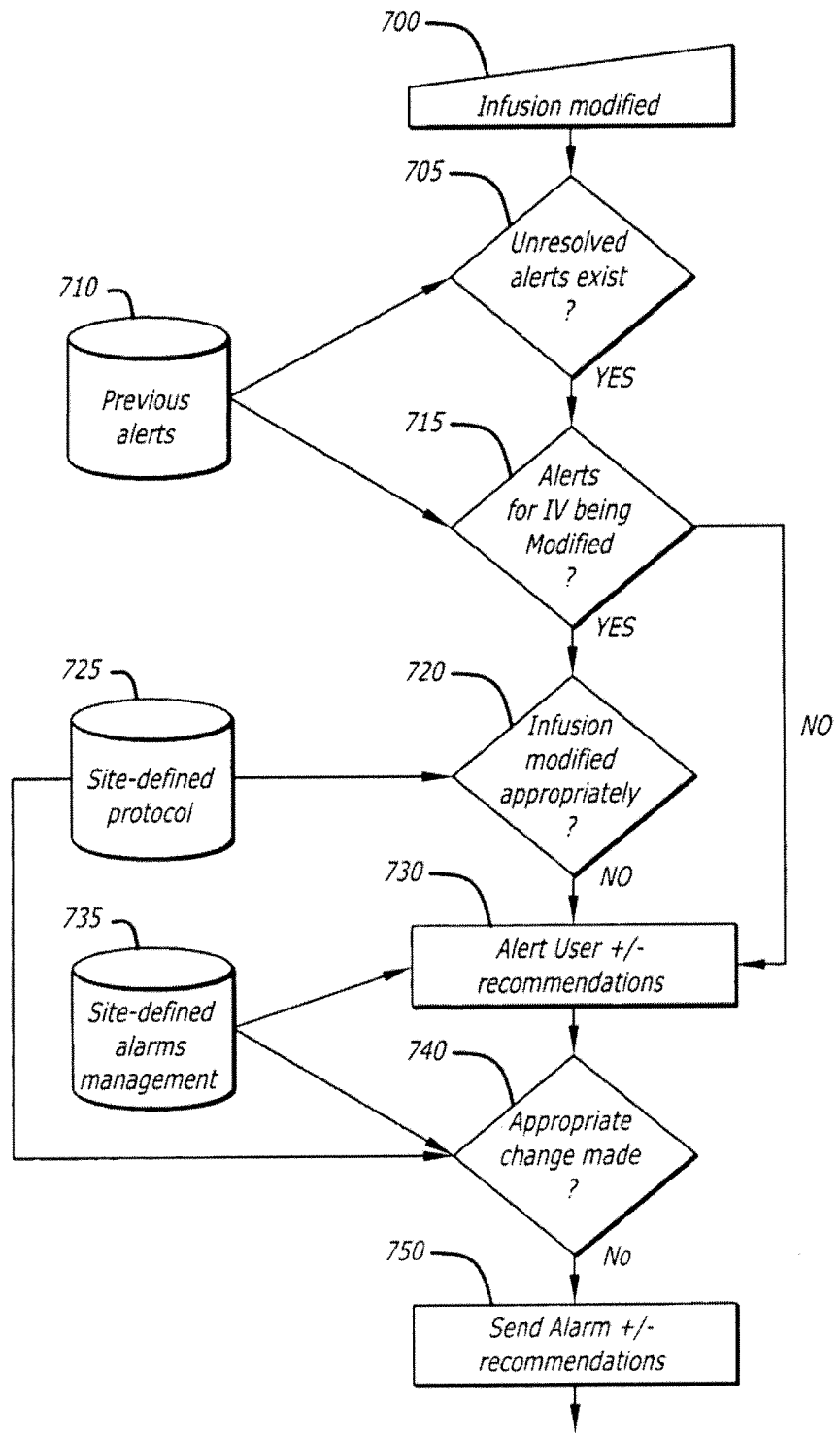
FIG. 12 is a flow chart illustrating one embodiment of the system of the present invention carried out by programming commands embodied in software running on the controllers, servers and information systems of the present invention that monitors infusions administering medications, detects when modifications to the running therapy protocol are made, determines if the modification is appropriate, and provides alerts and/or recommendations for correcting any inappropriate modifications.

In addition to receiving results from other institutional systems or clinical devices monitoring the condition of a patient, the results may also be received from the patient. For example, the patient could self-administer a pain scale by entering a response to a prompt provided to the patient by, for example, the user interface 235 of controller 200 (FIG. 2). The system may provide a notification to the patient at the appropriate time to enter the pain scale response, and provide an alarm as appropriate based upon the response by the patient, or a lack of response by the patient. Further alarms and/or recommendations are issued by the system in accordance with databases of site-defined protocols, rules, pharmacokinetic and/or pharmacodynamic equations, and alarms management rules and guidelines As indicated above, the system is programmed to check for any changes being made to a therapy during the course of therapy administration. For example, one embodiment of the system of the present invention is programmed to monitor all changes to infusion regimens that are made by care givers in an institution, as illustrated by the flow chart of FIG. 12. In this embodiment, an infusion is modified in box 700, such as, for example, by changing the rate of the infusion, the amount to be infused or other infusion parameter. The controller 200 (FIG. 2) sends a signal over the communication system indicating that a change to the infusion regimen has been made.

The system, monitoring the information flowing through the communication system, detects the signal that the infusion has been changed. It will be understood that the location of the program monitoring for changes and for analyzing the appropriateness of the changes is not important to the scope of the present invention. Such a program may be running on one or more servers, or the program may be running on the processor of controller 200.

As indicated by box 705, the system determines if any unresolved alerts exist by querying a database 710 or previous alerts associated with the therapy being administered to the patient. If unresolved alerts exist, the system determines whether they are alerts indicating that the infusion has been modified in box 715. If the unresolved alerts are determined to be alerts indicating a change in infusion, the system determines if the changes to the infusion are appropriate in box 720 by comparing the changes to a database of site-defined protocols, rules, guidelines, and/or pharmacokinetic and/or pharmacodynamic models or equations 725.

If the system determines that the infusion has not been modified appropriately in box 720, the system provides an alert to the care giver, which may also include one or more recommendations for correcting the inappropriate parameter of condition, in box 730. The system continues to monitor and determine if an appropriate changes was made in response to the alert in box 740. If an appropriate change has not been made, the system sends an alert or an alarm to the care giver or others in the institution in box 750. This alert or alarm may also include recommendations for correcting the condition causing the alert or alarm.

Referring again to box 715, if the system determines that the previous unresolved alert is not an alert associated with a modification of the infusion, the process jumps to box 730, where the system provides an alert, with or without recommendations, to the care giver or other in the institution. As before, the system then monitors to see if an appropriate change is made to correct the cause of the alert condition in box 740, and sends an alert or alarm, with or without recommendations for correcting the cause of the alert, to care givers or others in the institution in box 750.

As discussed previously with reference to FIG. 11, the system continues to monitor to determine if an appropriate response to the alert or alarm issued in box 750 is received. If not, then the system may escalate the priority or severity of the alert or alarm until the condition causing the alert or alarm is resolved.

At times, a clinician or other care giver may decide to override an alert or recommendation. In this situation, the system may be programmed to prompt the physician or care giver to enter a reason for the override. This prompt will typically be provided by, for example, a user interface, such as user interface 235 of controller 200 (FIG. 2). The clinician or care giver may either enter a reason by using alpha numeric keys provided by the interface, or, alternatively, may select a reason from a pre-determined list of reasons, such as may be provided in a drop down list or otherwise. This feature provides for documentation of the reason for the override which is then stored in the patient's eMAR. Besides the obvious use of this information in documenting the course of therapy administered to the patient, such information is also useful in that it may be retrieved and analyzed at a later time to assist the institution in modifying the institutionally determined rules, protocols, guidelines and models used by the system to monitor the course of therapy administered to the institution's patients to ensure that the rules and protocols reflect the best practices of the institution.

Similarly, the clinician or care giver may be prompted by the system to enter information about their perception of the utility of an alarm. This information may be used to adjust the alarms management protocols and rules used by institution.

When an alert occurs, the system records all appropriate patient information and care giver response to the alert, including, for example, the time for care giver to respond to the alert, the action taken, the reason for action, as well as the response of the patient to the change in therapy brought about by a correction to an alert or alarm condition, as determined by parameters being monitored by various clinical devices and/or values determined by laboratory tests or patient input. This information may also be analyzed by the system to assist in adjusting or modifying the institutionally determined protocols, rules, guidelines, and pharmacokinetic and pharmacodynamic models used by the system in monitoring and analyzing the delivery of therapy within the institution.

The therapy management system, utilizing the application modules described above, monitors the infusion process in a real-time manner, providing alerts on the appropriate video display screens located throughout the institution and allows intervention by nurses or other caregivers at remote locations if necessary. As described previously, the system may also, or instead, provide the alert to a pager, PDA, telephone, email or the like. If the pharmacy management system is directly linked to the therapy management system, the therapy management system may also provide a scheduling report to the pharmacy in determining the status of ongoing infusions, as well as in scheduling the preparing of medications for future infusions.

As can be readily understood by those skilled in the art, the various embodiments of the present invention provide useful solutions to a variety of therapy management problems. One aspect that is particularly useful is that the embodiments of the present invention provide the automatic monitoring, recording and reporting functions that enable not only implementation of critical pathway management plans, but ensure compliance with them as therapy is administered to a patient. For example, one of the current "core measures" of the Joint Commission on Accreditation of Healthcare Organizations (JCAHO) for the treatment of community-acquired pneumonia is that two blood cultures be drawn prior to administering the first dose of antibiotic. As described above, the therapy management system in accordance with the present invention may be programmed to identify when a patient is diagnosed with community acquired pneumonia, monitor the system for verification that blood has been drawn for laboratory tests, and then prompt a care giver attempting to administer an antibiotic that one or both of the blood draws has not been taken. Embedding the critical pathway into the therapy management software, databases and rules engines in accordance with the present invention ensures compliance of the critical pathway, and automatically collects information about the entire process of care involved in delivering the prescribed treatment regimen. Such information assists the institution in ensuring that the care prescribed is actually delivered, and will also assist the institution in justifying the cost of treatment, or "pay for performance" of the care provided by the institution.

In another embodiment, the present invention includes a "Code Mode" that allows a care-giver to bypass the system to immediately cause a list of drugs that have been preselected by the institution to be used in an emergency situation. The initiation of the "Code Mode" causes a time-stamp to be placed in the patient's eMAR along with the identity of the drug selected from the displayed list of drugs to be used to treat the emergency. This feature ensures that the emergency, and the treatment used to address the emergency, are accurately recorded in the patient's eMAR. This feature may also include suppression of all on-going alerts to prevent distraction of the care givers in the emergency situation.

Figure 13:
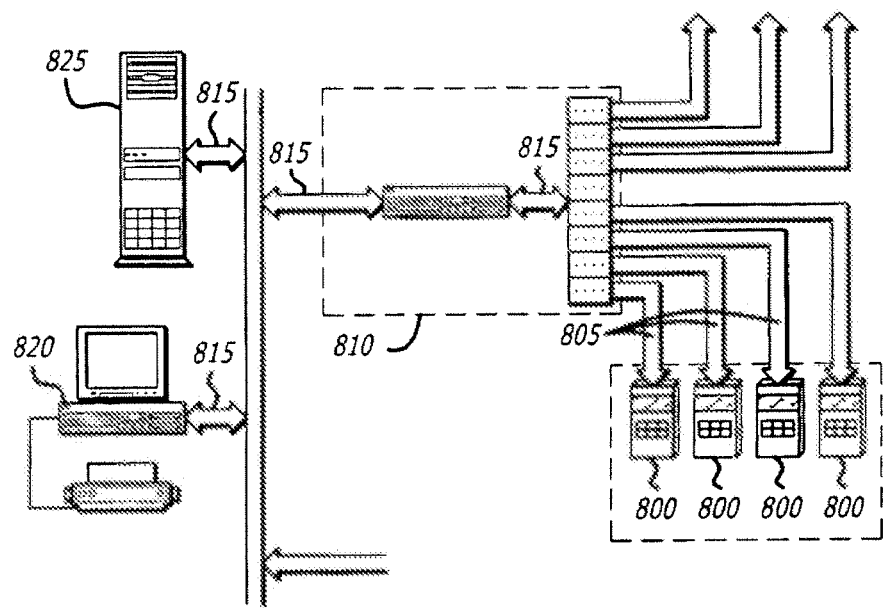
FIG. 13 is a graphical representation of another embodiment of the therapy management system of the present invention showing the clinical devices connected to a communications network through a data concentrator.

While one particular embodiment of the present invention has been described above, alternative configurations of the therapy management system network are possible. For example, one alternative embodiment of the therapy management system is depicted in FIG. 13. In this configuration, clinical devices 800 are connected by means of appropriate interfaces and cabling 805 to a bedside data concentrator 810 which would typically be located outside of a private room, semi-private room or ward area. In this configuration, there is no bedside computer or controller as described previously. Instead, the bedside data concentrator 810 is connected through an appropriate interface and cabling to the local area network 815, where the data gathered from the clinical devices 800 is then available for processing by the therapy management system and display at the various monitoring stations, such as either in the pharmacy or at the nurse station 820 or stored or further routed by a server 825. As described previously, the devices may also communicate with each other and the communication system 815 by wireless means.

Figure 14:
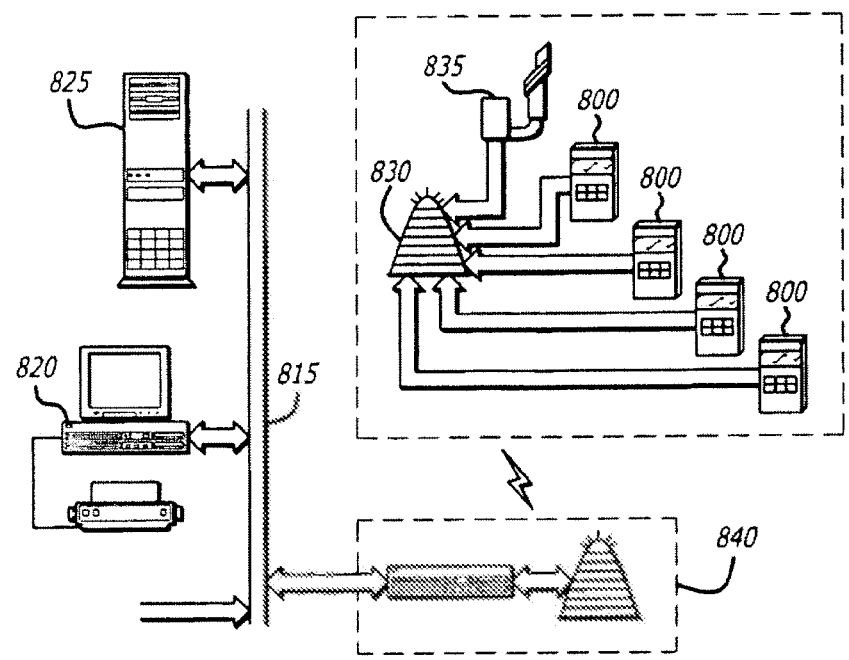
FIG. 14 is a graphical representation of still another embodiment of the therapy management system of the present invention showing clinical monitoring and/or medication delivery devices transmitting and receiving information from the communication system through a wireless communication system.

A further embodiment of the therapy management system local area network is depicted in FIG. 14. In this embodiment, the file server and monitoring stations are connected using appropriate interfaces and Ethernet cabling to an RF data concentrator 830. At the bedside locations in the private rooms, semi-private rooms or ward areas of the institution, the clinical devices 800 and barcode reader 835 at the bedside are connected to an RF transmitter/receiver 830. This RF transmitter/receiver 830 transmits the information gathered from the clinical devices 800 and the barcode reader 835 to the RF data concentrator 840 attached to the local area network 815. Thus, expensive cabling is not required to connect every patient treatment area. Additionally, flexibility in locating the clinical devices 800 and barcode reader 835 is obtained as well as allowing the ability to reconfigure the patient treatment area without costly rewiring of the Ethernet cabling.

Figure 15:
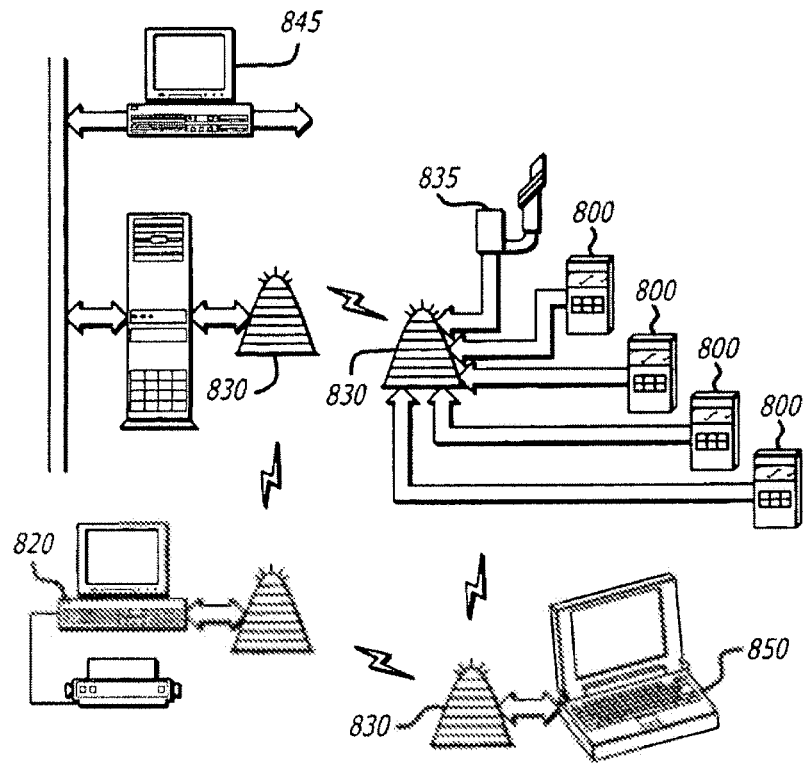
FIG. 15 is a graphical representation of another embodiment of the therapy management system of the present invention showing a communication system where all connections are wireless.

Yet another embodiment of the therapy management system local area network 815 configuration is shown in FIG. 15. In this configuration, the Ethernet cabling connecting the pharmacy stem (not shown), bed side computer or controller 845, the nurse station 820 and bedside computers or controllers and clinical devices 800 is eliminated entirely. Each hardware element, comprising the file server, nursing station, pharmacy station and bedside computer or controller and clinical devices and/or barcode readers is connected to an RF transmitter/receiver 830. In this manner, all of the information is transmitted throughout the local area network 815 by way of radio transmission rather than by using costly network cabling. Such a system would additionally allow for the use of portable computers 850, PDAs, smart cards and other devices, such as portable medication data carriers having RF transmitter/receivers 830 or other means of wireless communication, as have been described above, that could then be carried with physicians, nurses or technicians as they circulate through the institution. With this configuration, care giving personnel could access the therapy management system either spontaneously or upon notification of an alert or alarm no matter where they were in the institution at any given time. Such a system would be particularly useful in a large institution where care giving personnel are likely to be responsible for many hospital beds or when personnel are out of the area or off the floor.

Figure 16:
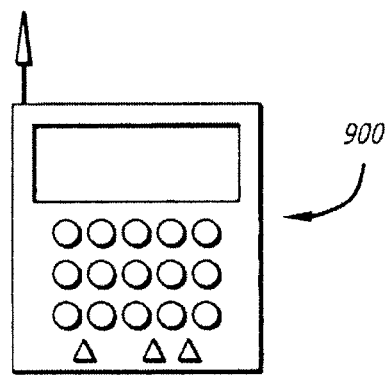
FIG. 16 is a graphical representation of yet another embodiment of the therapy management system of the present invention showing a hand held device configured to communicate with an institutions information systems using a wireless communication system for entering patient data and for receiving and displaying alerts or recommendations to a care giver.

In accordance with aspects of the present invention, a medication database carrier ("MDC") 900, one embodiment of which is depicted in FIG. 16, including a processor and a memory for storing information is provided to monitor medication parameters or other information used by a nurse or other care-giver to program a medication administration device to deliver medication to a patient. Various types of information may be stored in the memory of the MDC 900, including databases containing information about drug interactions and possible contraindications and/or side-effects of medications, and a library or libraries of established guidelines for the administration of various medications. For example, the guidelines may include institutionally-established guidelines or limits on drug administration parameters, such as dosage, frequency of administration, and other delivery related information such as, for example, appropriate flow rates and infusion durations for programming infusion pumps. Additionally, the guidelines may encompass guidelines for providing drug administration appropriate to a particular patient or to treatment areas having different sets of delivery parameters for similar medications, such as medication administration directed to geriatric, pediatric, and oncology patients. Guidelines may also be included that are directed to particular therapy regimens, such as chemotherapy regimens or regimens for treating chronic infection or pain. The term "database" or "data base" as used herein will be understood by those skilled in the art to be used as is commonly understood, that is, the term "data base" refers to a collection of values or information organized, formatted, and stored in such a manner as to be capable of being retrieved and analyzed using an appropriate program contained in software or other form.

In one embodiment of the present invention, the MDC 900 may be interfaced to the nurse station system 135 (FIG. 1) or any other of the information systems of the central system of an institution through a cradle or other docking device that provides a connection between the MDC 900 and the therapy management system. This information may then be processed and stored on the therapy management system, or the information may be communicated by the therapy management system to various other institutional information systems over the communication system 50. In this manner, information from the pharmacy information system 20, for example, may be communicated through the communication system 50, the nurse station system 135, and the MDC cradle into the MDC 900. Similarly, information contained within the MDC 900 may be communicated through the MDC cradle, the nurse station computer system 135, and the communication system 50 to any of the other systems of the institution. Alternatively, the MDC may be capable of wireless communication with any or all of the institution's systems.

The medical database carrier 900 generally refers to a device that contains medication and/or patient specific information and/or databases or libraries, including institutionally generated guidelines for the delivery of medication to a patient, as well as drug interaction information or information concerning possible drug side-effects, and that is portable such that it can be carried by a nurse or other care-giver to and from a patient's bedside. Alternatively, as will be described in more detail below, the MDC 900 may be considered to be relatively stationary in that it is associated with either a particular patient or medication administration device. The MDC 900 may also have a storage capability and technology for interfacing with a computer system or network so that information may be communicated between the MDC 900 and other devices, such as computers, medication administration devices, clinical devices such as vital signs monitoring devices and the like. The MDC may also have a video display screen in color or black and white (mono-color), such as that provided by an LCD or an array of LED's, or other, and a data entry means such as a keyboard, keypad, a screen used for handwriting recognition, or other data entry means.

A general concept embodied in the MDC 900 is to provide a system and method wherein medication administration parameters or other information entered into a medication administration device such as an infusion pump, may be retrieved from the device prior to actual medication administration and compared to information in the database or databases stored in the MDC to determine if the entered parameters or information fall within institutionally established guidelines for the administration of a particular medication. If the comparison indicates that the parameters or information entered into the medication administration device are appropriate in that they fall within the established guidelines, then an indication to that effect is provided to the nurse or care-giver and the nurse may then begin medication administration.

Alternatively, if the comparison indicates that one or more parameters or information do not meet the established guidelines, a warning or alert is provided to the nurse or care-giver that one or more parameters or a portion of information has been incorrectly entered into the medication administration device, and that corrective action or an override is required before medication administration can begin. In another embodiment, the medication administration device may be automatically inhibited from starting administration of a medication unless it receives a signal from the MDC 900 that the comparison was favorable, thus providing a fail-safe against incorrect administration of the medication.

The MDC 900 typically will also be capable of retrieving medication administration parameters or information from a medication administration device, and storing data or information concerning various transactions in its memory representing the identity and treatment regimens for medications given to a patient, as well as other information, such as care-giver identity, equipment location, patient vital signs information, or any other information sought to be recorded. The MDC 900 may also store data or information concerning primary or secondary validation of previous and/or duplicate transactions of medical treatment information. The display of the MDC may also provide a care-giver with messages or other information, such as warnings or prompts to enter data, related to medication administration. Moreover, the keyboard or other information entry means of the MDC may be used for manually entering information into the MDC for storage in the memory of the MDC.

While specific examples of an MDC 900 are set forth herein, it will be understood that the MDC is meant to include any device that carries out the basic concept of the invention. That is, a device that receives medication administration or treatment information from a medication administration device, such as, for example, but not limited to, an infusion pump, and has a processor capable of comparing the received information to institutionally established medication administration guidelines or other pertinent information or data, such as drug interaction information and/or a library of possible side-effects, and then providing an indication of the result of the comparison to a nurse or care-giver before administration of a medication to a patient is begun, will accomplish the aims of the present invention. A particularly advantageous embodiment includes storing information about the medication administration, such as the medication administration or treatment parameters, and/or other information, such as the identity of the patient and care-giver, in the memory of the MDC 900 until the MDC 900 re-establishes a communication connection with the therapy management system, whereby the information stored in the memory of the MDC 900 may be communicated to the therapy management system and incorporated into one or more of an institution's information databases. Updating the databases provides a verification that the treatment has been rendered thereby avoiding a duplicate treatment. In this manner, the present invention "closes the loop" ensuring that the right medication has been given in the right manner to the right patient.

For example, consistent with the present invention, the MDC 900 may be embodied in a hand-held personal digital assistant (PDA) such as a Palm™ Pilot or any PDA running either the Palm™ operating system, the Windows™ operating system or an equivalent, a desktop computer, a notebook computer, or other portable computer system. The MDC may also comprise a smartcard such as those that are capable of processing and storing data, such as the American Express Bluecard. The use of such devices is advantageous in that devices having a suitably large memory to accommodate the type of information required by the present invention to monitor and track medication administration information and validate treatment as well as retrieving other patient information, are readily available and relatively inexpensive, thus allowing an MDC to be assigned to each individual patient, or alternatively, to an individual medication administration device, such as an infusion pump, or other clinical device, such as a vital signs monitor. Additionally, such devices are small, compact and easily transportable.

Alternatively, the MDC 900 may be embodied in any device that includes an active embedded processor and a memory capable of storing information. Such an active embedded processor may be even smaller and more portable than a PDA or notebook computer. For the purposes of the present invention, such an active embedded processor includes any device incorporating a microprocessor and allows for input and/or output of information, whether via electrical, radio frequency, or optical means, wireless or direct contact, and which contains its own power supply. One example of an active embedded processor in accordance with this invention may be attached to or embedded in the packing or container of a medication to be delivered to a patient. Such devices may typically be manufactured no larger than, for example, a postage stamp or business card and yet include, using micro circuitry, enough processing power, information storage, data or information input and output, and power to be suitable for use as a medical database carrier. Alternatively, the embedded processor and memory may be integrated into a medication administration device, such as an infusion pump or other device.

In another embodiment, such as where the patient specific asset or medication administration device is modular and includes a controller such as in the ALARIS Medical Systems, Inc. MEDLEY™ MEDICATION SAFETY SYSTEM, the controller may include sufficient programming to perform the function of an MDC. In such case, the controller would be in contact with institutional information systems, such as the pharmacy information system 20, and receive updated information concerning institutional guidelines for medication administration or other patient area or drug specific information to be used to compare with entered medication administration information or parameters before beginning administration of a medication to a patient.

It is not unusual at present to find patient stations having a computer or bedside controller 55 (FIG. 1) located at patient bedsides in a care-giving facility. Such bedside controllers 55 may serve a single patient, or may serve more than one patient, depending on the design and arrangement of the patient area. There may also be a variety of equipment or clinical devices attached to the bedside controller 55. Examples of such devices are a bar code reader, a printer (not shown), patient monitoring equipment for monitoring patient vital signs, or other patient specific assets (PSA) assigned to the patient. Further examples of such a PSA include an infusion device 75 such as can form a part of the ALARIS Medical Systems, Inc.'s MEDLEY™ MEDICATION SAFETY SYSTEM 55. Attention is directed to U.S. Pat. No. 5,713,856 entitled "Modular Patient Care System" to Eggers et al. in which the controller is described as an advanced interface unit, and is incorporated herein by reference. In such system, an infusion device may be mounted to the controller. Other devices, such as a vital signs monitor or monitors, are envisioned as being mountable to the controller also. Other infusion or drug delivery devices and/or patient monitoring equipment such as cardiac or respiratory monitors may also comprise or form a part of the PSA.

The bedside equipment and clinical devices are typically equipped with data communication technology such as RS 232 serial ports or proprietary communication ports that allow information and data to be communicated to and from the equipment or clinical device. Using this communication technology, the bedside equipment and clinical devices may be connected to the bedside controller 55, or, alternatively, they may be connected, either by wire or wireless system, to the facility communication system 50 using wireless technology, such as RF, IR, or other wireless communication protocols.

While the therapy management system has been described above in terms of controlling and analyzing information flow to and from an infusion pump, devices incorporating the principles of the present invention include, for example, and not limited to, vital signs monitors or other clinical devices interacting with a patient. For example, the medication administration device may also be a patient feeding device.

Furthermore, the institutional communication system 50 as mentioned above numerous times is not meant to be taken in a limited sense. Such a communication system may encompass an entire hospital facility or may be located only in a small area of the hospital. It may also include a communication system in a care-giving facility other than a hospital and may have application to an alternate care facility, such as a patient's home. The above embodiments are described for exemplary purposes only.

In the above detailed description, well-known devices, methods, procedures, and individual components have not been described in detail so as not to obscure aspects of the present invention. Those skilled in the art will understand those devices, methods, procedures, and individual components without further details being provided here. Moreover, while the embodiments disclosed above are described for use in a hospital environment, it will be understood that the system and method may be useful in other environments as well, such as outpatient clinics and other environments where care is delivered to a patient.

While several particular forms of the invention have been illustrated and described, it will be apparent that various modifications can be made without departing from the spirit and scope of the invention.

We claim:

1. A system for managing a therapy provided to a patient, comprising:
   a medication delivery device configured for two-way communication with at least one of a monitoring device and an institutional information system, wherein the medication delivery device adjusts the delivery of a drug, medication or fluid to a patient based on institutionally determined rules related to patient specific information; and
   a processor configured to provide an alert when the delivery of the drug, medication or fluid violates one of the institutionally determined rules, and configured to increase a priority of the alert when a status of the alert has not changed for a selected period of time.

2. The system of claim 1, wherein the institutional rules comprise at least one of a drug, medication, or fluid dosing parameters and rules, device operating characteristics, or device communication parameters.

3. The system of claim 1, wherein the medication delivery device is in direct communication with the monitoring device.

4. The system of claim 1, wherein the processor is further configured to transmit instructions to automatically adjust, or direct the adjustment of, the delivery of the drug, medication or fluid to bring delivery of said drug, medication or fluid within the institutional rules.

5. The system of claim 1, wherein the patient specific information comprises at least one of a physiological data, or a laboratory data.

6. A system for managing a therapy to be provided to a patient, comprising:
   a memory comprising a database capable of storing and accepting a patient specific data and a configurable database for institutionally determined rules that define dosing parameters as a function of the patient specific data; and
   a processor coupled to the memory, the processor configured to execute commands stored in the memory, causing the system to:
      select a first dosing regimen for a drug, medication or fluid based on the therapy and a first set of the patient specific data;
      accept a second set of patient specific data;
      compare the second set of patient specific data with the institutionally determined rules; and
      when the first dosing regimen violates an institutionally determined rule based on the second set of patient specific data, to automatically adjust, or direct the adjustment of, the delivery of the drug, medication or fluid to bring delivery of said drug, medication or fluid within the institutionally determined rules, and to provide an alert; and further causing the system to:
      increase a priority of the alert when a status of the alert has not changed for a selected period of time.

7. The system of claim 6, wherein the commands stored in the memory further cause the system to receive a recommendation to alter at least one institutionally determined rule.

8. The system of claim 7, wherein the recommendation to alter at least one institutionally determined rule is based on an institution providing the therapy to the patient.

9. The system of claim 6, wherein the commands stored in the memory further cause the system to adjust the therapy to be provided to the patient based on the second set of patient specific data.

10. The system of claim 6, wherein the institutionally determined rules comprise drug dosing parameters, device operating characteristics, device communication parameters, and identification (ID) values for a plurality of patients.

11. The system of claim 6, wherein the institutionally determined rules comprise a model for the first medication concentration as a function of time in a plurality of compartments of a patient's body.

12. The system of claim 6, wherein the institutionally determined rules comprise a model that relates a concentration of the drug, medication or fluid with a physiological response of the patient.

13. The system of claim 6, wherein the commands stored in the memory further cause the system to communicate to a medical care device an instruction to monitor a concentration of the drug, medication or fluid in a compartment of the patient's body.

14. A system for managing a therapy to be provided to a patient, comprising:
   a memory comprising a database capable of storing and accepting a patient specific data and a configurable database for institutionally determined rules that define dosing parameters as a function of the patient specific data; and
   a processor coupled to the memory, the processor configured to execute commands stored in the memory, causing the system to:
      accept a set of patient specific data during delivery of a drug, medication, or fluid according to a first dosing regimen;
      compare the set of patient specific data with the institutionally determined rules;
      when the first dosing regimen violates an institutionally determined rule based on the set of patient specific data, to automatically adjust, or direct the adjustment of, the delivery of the drug, medication or fluid to bring delivery of said drug, medication or fluid within the institutionally determined rules and to provide an alert; and further causing the system to:
      increase a priority of the alert when a status of the alert has not changed for a selected period of time.

15. The system of claim 14, wherein the commands stored in the memory further cause the system to receive a recommendation to alter at least one institutionally determined rule.

16. The system of claim 15, wherein the recommendation to alter at least one institutionally determined rule is based on an institution providing the therapy to the patient.

17. The system of claim 14, wherein the commands stored in the memory further cause the system to adjust the therapy to be provided to the patient based on the set of patient specific data.

18. The system of claim 14, wherein the institutionally determined rules comprise drug dosing parameters, device operating characteristics, device communication parameters, and identification (ID) values for a plurality of patients.

19. The system of claim 14, wherein the institutionally determined rules comprise a model for the first medication concentration as a function of time in a plurality of compartments of a patient's body.

20. The system of claim 14, wherein the institutionally determined rules comprise a model that relates a concentration of the drug, medication or fluid with a physiological response of the patient.

21. The system of claim 14, wherein the commands stored in the memory further cause the system to communicate to a medical care device an instruction to monitor a concentration of the drug, medication or fluid in a compartment of the patient's body.

* * * * *